United States Patent
Winqvist et al.

(12)

(10) Patent No.: US 10,502,736 B2
(45) Date of Patent: Dec. 10, 2019

(54) TREATING MULTIPLE SCLEROSIS

(71) Applicant: TLA TARGETED IMMUNOTHERAPIES AB, Stockholm (SE)

(72) Inventors: Ola Winqvist, Uppsala (SE); Graham Cotton, Edinburgh (GB)

(73) Assignee: TLA TARGETED IMMUNOTHERAPIES AB, Stockholm (SE)

( * ) Notice: Subject to any disclaimer, the term of this patent is extended or adjusted under 35 U.S.C. 154(b) by 0 days.

(21) Appl. No.: 15/629,697

(22) Filed: Jun. 21, 2017

(65) Prior Publication Data
US 2018/0038857 A1 Feb. 8, 2018

Related U.S. Application Data

(60) Division of application No. 14/105,628, filed on Dec. 13, 2013, now Pat. No. 9,726,666, which is a continuation-in-part of application No. PCT/GB2012/051357, filed on Jun. 13, 2012, and a continuation-in-part of application No. PCT/GB2012/051349, filed on Jun. 13, 2012, and a continuation-in-part of application No. PCT/GB2012/051348, filed on Jun. 13, 2012, and a continuation-in-part of application No. PCT/GB2012/051351, filed on Jun. 13, 2012, and a continuation-in-part of application No. PCT/GB2012/051350, filed on Jun. 13, 2012, and a continuation-in-part of application No. PCT/GB2012/051355, filed on Jun. 13, 2012, and a continuation-in-part of application No. PCT/GB2012/051345, filed on Jun. 13, 2012, and a continuation-in-part of application No. PCT/GB2012/051352, filed on Jun. 13, 2012, and a continuation-in-part of application No. PCT/GB2012/051346, filed on Jun. 13, 2012, and a continuation-in-part of application No. PCT/GB2012/051353, filed on Jun. 13, 2012, and a continuation-in-part of application No. PCT/GB2012/051356, filed on Jun. 13, 2012, and a continuation-in-part of application No. PCT/GB2012/051354, filed on Jun. 13, 2012.

(60) Provisional application No. 61/496,442, filed on Jun. 13, 2011, provisional application No. 61/496,167, filed on Jun. 13, 2011, provisional application No. 61/496,288, filed on Jun. 13, 2011, provisional application No. 61/496,242, filed on Jun. 13, 2011, provisional application No. 61/496,209, filed on Jun. 13, 2011, provisional application No. 61/496,195, filed on Jun. 13, 2011, provisional application No. 61/496,228, filed on Jun. 13, 2011, provisional application No. 61/496,264, filed on Jun. 13, 2011, provisional application No. 61/496,184, filed on Jun. 13, 2011, provisional application No. 61/496,329, filed on Jun. 13, 2011, provisional application No. 61/496,377, filed on Jun. 13, 2011, provisional application No. 61/496,352, filed on Jun. 13, 2011.

(51) Int. Cl.
| | |
|---|---|
| *A61K 39/00* | (2006.01) |
| *A61K 39/395* | (2006.01) |
| *A61K 39/40* | (2006.01) |
| *A61M 37/00* | (2006.01) |
| *G01N 33/566* | (2006.01) |
| *A61M 1/36* | (2006.01) |
| *G01N 33/569* | (2006.01) |

(52) U.S. Cl.
CPC ......... *G01N 33/566* (2013.01); *A61M 1/3618* (2014.02); *A61M 1/3679* (2013.01); *G01N 33/56972* (2013.01); *G01N 2333/70596* (2013.01); *G01N 2333/7158* (2013.01); *G01N 2800/065* (2013.01)

(58) Field of Classification Search
None
See application file for complete search history.

(56) References Cited

U.S. PATENT DOCUMENTS

| 8,658,377 B2 | 2/2014 | Lillard et al. |
| 2003/0017979 A1 | 1/2003 | Mack |
| 2003/0215421 A1 | 11/2003 | McDonald |

(Continued)

FOREIGN PATENT DOCUMENTS

| DE | 102005036505 A1 | 6/2006 |
| EP | 1255112 A2 | 11/2002 |

(Continued)

OTHER PUBLICATIONS

Mahad et al. 2003. Seminars in Imunology. 15:23-32 (Year: 2003).*

(Continued)

*Primary Examiner* — Shulamith H Shafer
(74) *Attorney, Agent, or Firm* — Michael Best & Friedrich LLP

(57) ABSTRACT

A method for treating multiple sclerosis comprises applying peripheral blood from a patient or subject to an apheresis column loaded with a solid support comprising one or more binding reagents capable of specifically binding to a chemokine receptor, optionally the chemokine receptor CCR2, CCR6, CCR3, CCR5, CCR1, CXCR3 and/or CCR9 immobilized directly or indirectly on the support thus removing one or more chemokine receptor, optionally CCR2, CCR6, CCR3, CCR5, CCR1, CXCR3 and/or CCR9 expressing cells from the peripheral blood of the patient or subject. Various companion diagnostic methods and useful binding reagents are also described.

9 Claims, 14 Drawing Sheets

Specification includes a Sequence Listing.

(56) References Cited

U.S. PATENT DOCUMENTS

| | | |
|---|---|---|
| 2004/0077835 A1 | 4/2004 | Offord |
| 2007/0092484 A1 | 4/2007 | Levine |
| 2009/0196823 A1 | 8/2009 | Cornelius et al. |
| 2010/0029753 A1 | 2/2010 | Anderson |
| 2011/0081407 A1 | 4/2011 | Lillard et al. |

FOREIGN PATENT DOCUMENTS

| | | |
|---|---|---|
| EP | 1783227 A1 | 5/2007 |
| EP | 2067495 A1 | 6/2009 |
| EP | 2118060 B1 | 10/2010 |
| WO | WO-0125492 A1 | 4/2001 |
| WO | WO-0140306 A1 | 6/2001 |
| WO | WO-2004026893 A2 | 4/2004 |
| WO | WO-2004045526 A2 | 6/2004 |
| WO | WO-050088 A2 | 1/2005 |
| WO | WO-2005037305 A1 | 4/2005 |
| WO | 2005/084667 | 9/2005 |
| WO | WO-2006052723 A2 | 5/2006 |
| WO | WO-2006125201 A2 | 11/2006 |
| WO | WO-2006126209 A1 | 11/2006 |
| WO | WO-2007024705 A2 | 3/2007 |
| WO | 2007/053082 | 5/2007 |
| WO | WO-2007133147 A1 | 11/2007 |
| WO | WO-2008059066 A1 | 5/2008 |
| WO | WO-2008142405 A1 | 11/2008 |
| WO | WO-2010021697 A2 | 2/2010 |
| WO | WO-2010029317 A2 | 3/2010 |
| WO | WO-2010103517 A1 | 9/2010 |
| WO | WO-2010142952 A2 | 12/2010 |
| WO | WO-2011017120 A1 | 2/2011 |
| WO | WO-2012112724 A1 | 8/2012 |

OTHER PUBLICATIONS

Izikson et al. 2000. J. Exp. Med. 192:1075-1080 (Year: 2000).*
Xia et al. 2009. Expert Opinion on Therap. Patents 19:295-303 (Year: 2009).*
Allen, et al., "A Rapid and Efficient Way to Obtain Modified Chemokines for Functional and Biophysical Studies", Cytokine, vol. 55, No. 2, May 2, 2011, 168-173.
An, et al., "Immunohistochemical Detection of CCR2 and CX3CR1 in Sepsis-Induced Lung Injury", Forensic Science International, Nov. 20, 2009, e21-e25.
Autschbach, et al., "Expression of Chemokine Receptors in Normal and Inflamed Human Intestine, Tonsil, and Liver", Cellular Immunology, vol. 236, Sep. 23, 2005, 110-114.
Bellani, et al., "Altered MRNA Levels of Chemokines and Cytokines in Schizophrenia and Bipolar Disorder", Schizophrenia Research, vol. 117, No. 2-3, Apr. 1, 2010, 251-252.
Beumer, et al., "Increased Level of Serum Cytokines, Chemokines and Adipokines in Patients with Schizophrenia is Associated with Disease and Metabolic Syndrome", Psychoneuroendocrinology, Apr. 1, 2012, 1901-1911.
Borchers, et al., "Lymphocyte Recruitment and Homing to the Liver in Primary Biliary Cirrhosis and Primary Sclerosing Cholangitis", Seminars in Immunopathology, vol. 31, No. 3, Jun. 17, 2009, 309-322.
Bossink, et al., "Plasma Levels of the Chemokines Monocyte Chemotactic Protein-1 and -2 are Elevated in Human Sepsis", Blood, vol. 86, No. 10, Nov. 15, 1995, 3841-3847.
Cancello, et al., "Review Article: Is Obesity an Inflammatory Illness? Role of Low-Grade Inflammation and Macrophage Infiltration in Human White Adipose Tissue", BJOG: An International Journal of Obstetrics and Gynecology, vol. 113, No. 10, Oct. 1, 2006, 1141-1147.
Chantry, et al., "Chemokines in Allergy", Current Drug Targets—Inflammation & Allergy, vol. 1, No. 1, Jan. 1, 2002, 109-116.
Charo, et al., "Chemokines in the Pathogenesis of Vascular Disease", Circulation Research, vol. 95, No. 9, Oct. 29, 2004, 858-866.
Chinese Office Action for Chinese Patent Application No. 2012800396667, English translation only provided to Applicant, dated Jun. 17, 2015, 8 pages.
Coillie, et al., "Functional Comparison of Two Human Monocyte Chemotactin Protein-2 Isoforms, Role of the Amino-Terminal Pyroglutamic Acid and Processing by CD26/Dipeptidyl Peptidase IV", Biochemistry, vol. 37, No. 36, Jan. 1, 1998, 12672-12680.
De Boer, et al., "Cytokines and Therapy in COPD: A Promising Combination?", Chest, vol. 121, No. 90050, May 1, 2002, 209S-218.
Eksteen, et al., "Hepatic Endothelial CCL25 Mediates the Recruitment of CCR9+ Gut-Homing Lymphocytes to the Sclerosing Cholangitis", Journal of Experimental Medicine, vol. 200, No. 11, Dec. 6, 2004, 1511-1517.
European Office Action for European Patent Application No. 1272680.6, dated Mar. 16, 2015, 6 pages.
European Office Action for European Patent Application No. 12727915.6, dated Oct. 13, 2015, 3 pages.
European Search Report for European Patent Application No. 12727921, dated May 24, 2016, 4.
Feng, "Involvement of a Novel Chemokine Decoy Receptor CCX-CKRin Breast Cancer Growth Metastasis and Patient Survival", Clinical Cancer Research, vol. 15, No. 9, May 1, 2009, 2962-2970.
Grant, et al., "Hepatic Expression of Secondary Lymphoid Chemokine (CCL21) Promotes the Development of Portal-Associated Lymphoid Tissue in Chronic Inflammatory Liver Disease", American Journal of Pathology, vol. 160, No. 4, Apr. 2002, 1445-1455.
Hanai, et al., "The Mode of Actions of Adacolumn Therapeutic Leucocytapheresis in Patients with Inflammatory Bowel Disease: A Concise Review", Clinical & Experimental Immunology, vol. 163, No. 1, Nov. 16, 2010, 50-58.
Hsing-Cheng, et al., "Immunologic Variables in Acute Mania of Bipolar Disorder", Journal of Neuroimmunology, vol. 150, No. 1-2, May 1, 2004, 116-122.
Hu, "Schizophrenia is a TH2 Dominant Autoimmune Disease Possibly Against Acetylcholine Receptors of CNS", ViXra.org, vol. 1204, Apr. 30, 2012, 0070.
Iarlori, et al., "Interferon beta-1b Modulates MCP-1 Expression and Production in Relapsing-Remitting Multiple Sclerosis", Journal of Neuroimmunology, vol. 123, No. 1-2, Feb. 1, 2002, 170-179.
International Search Report and Written Opinion for PCT/GB2012/051345, dated Jan. 11, 2013, 24 pages.
International Search Report and Written Opinion for PCT/GB2012/051346, dated Jan. 11, 2013, 22 pages.
International Search Report and Written Opinion for PCT/GB2012/051348, dated Jan. 11, 2013, 23 pages.
International Search Report and Written Opinion for PCT/GB2012/051353, dated Jan. 11, 2013, 22 pages.
International Search Report and Written Opinion for PCT/GB2012/051355, dated Jan. 11, 2013, 22 pages.
International Search Report for PCT/GB2012/051349, dated Jan. 2, 2013, 7 pages.
International Search Report for PCT/GB2012/051350, dated Jan. 11, 2013, 6 pages.
International Search Report for PCT/GB2012/051351, dated Jan. 2, 2013, 5 pages.
International Search Report for PCT/GB2012/051352, dated Jan. 11, 2013, 7 pages.
International Search Report for PCT/GB2012/051354, dated Jan. 11, 2013, 7 pages.
International Search Report for PCT/GB2012/051356, dated Jan. 11, 2013, 6 pages.
International Search Report for PCT/GB2012/051357, dated Nov. 19, 2012, 6 pages.
Iwamoto, et al., "Molecular Aspects of Rheumatoid Arthritis: Chemokines in the Joints of Patients", FEBS Journal, vol. 275. No. 18, Sep. 1, 2008, 4448-4455.
Kruszynski, et al., "Synthetic, Site-Specific Biotinylated Analogs of Human MCP-1", Journal of Peptide Science, vol. 12, May 1, 2006, 354-360.
Linton, et al., "CCR9-Expressing CD14+HLA-DRhi Blood Monocytes Promote Intestinal Inflammation in IBD", Journal of Translational Medicine, vol. 9, No. Supply 2, Nov. 23, 2011, p. 32.

(56) References Cited

OTHER PUBLICATIONS

Liu, et al., "Correlation Effect of EGFR and CXCR4 and CCR7 Chemokine Receptors in Predicting Breast Cancer Vletastasis and Prognosis", Journal of Experimental & Clinical Cancer Research, vol. 29, No. 16, 2010, 9 pages.

Lumeng et al. "Obesity Induces a Phenotypic Switch in Adipose Tissue Macrophage Polarization", Journal of Clinical Investigation, American Society for Clinical Investigation, vol. 117, No. 1, Jan. 1, 2007, 175-184.

Maury, et al., "Adipokine Dysregulation, Adipose Tissue Inflammation and Metabolic Syndrome", Molecular and Cellular Endocrinology, vol. 314, No. 1, Jan. 15, 2010, 1-16.

Nakajima, "Increased Intrathecal Chemokine Receptor CCR2 Expression in Multiple Sclerosis", Biomarker Insights, Jan. 1, 2007, 463.

Nakatani, et al., "CCR4+ Memory CD4+ T Lymphocytes are Increased in Peripheral Blood and Lesional Skin from Patients with Atopic Dermatitis", Journal of Allergy and Clinical Immunology, vol. 107, No. 2, Feb. 1, 2001, 353-358.

Niu, et al., "Role of MCP-1 in Cardiovascular Disease: Molecular Mechanisms and Clinical Implications", Clinical Science, vol. 117, No. 3, Aug. 2009, 95-109.

Pease, et al., "Asthma, Allergy and Chemokines", Current Drug Targets, vol. 7, No. 1, retrieved from the Internet on Sep. 13, 2012: http://www.benthamdirect.org/pages/article/1/117/asthma-allergy-and-chemo- kines.html, Jan. 1, 2006, 3-12.

Petrek, et al., "CC and C Chemokine Expression in Pulmonary Sarcoidosis", European Respiratory Journal, vol. 20, No. 5, Nov. 1, 2002, 1206-1212.

Reale, et al., "Dysregulation of Chemo-Cytokine Production in Schizophrenic Patients Versus Healthy Controls", BMC Neuroscience, Biomed Central, vol. 12, No. 1, Jan. 25, 2011, 13 pages.

Reape, et al., "Chemokines and Atherosclerosis", Atherosclerosis, vol. 147, No. 2, Dec. 1, 1999, 213-225.

Rottman, et al., "Potential Role of the Chemokine Receptors CXCR3, CCR4, and the Integrin AlphaEbeta7 in the Pathogenesis of Psoriasis Vulgaris", Laboratory Investigation, vol. 81, No. 3, Mar. 2001, 335-347.

Sarafi, et al., "Murine Monocyte Chemoattractant Protein (MCP)-5: A Novel CC Chemokine that is a Structural and Functional Homologue of Human MCP-1", Journal of Experimental Medicine, vol. 185, No. 1, Jan. 1, 1997, 99-110.

Souto, et al., "Essential Role of CCR2 in Neutrophil Tissue Infiltration and Multiple Organ Dysfunction in Sepsis", American Journal of Respiratory and Critical Care Medicine, vol. 183, No. 2, Jan. 15, 2011, 234-242.

Speyer, "Novel Chemokine Responsiveness and Mobilization of Neutrophils During Sepsis", American Journal of Pathology, vol. 165, No. 6, Dec. 2004, 2187-2196.

Takanami, "Overexpression of CCR7 mRNA in Nonsmall Cell Lung Cancer: Correlation with Lymph Node Metastasis", International Journal of Cancer, vol. 105, No. 2, Jun. 10, 2003, 186-189.

Teixeira, et al., "Increased Serum Levels of CCL11/eotaxin in Schizophrenia", Progress in Neuro-Psychopharmacology & Biological Psychiatry, vol. 32, No. 3, Nov. 23, 2007, 710-714.

Terada, et al., "Stromal Cell-Derived Factor-1 from Biliary Epithelial Cells Recruits CXCR4-Positive Cells: Implications for Inflammatory Liver Disease", Laboratory Investigation, vol. 83, No. 5, May 1, 2003, 665-672.

Teraki, et al., "Homing Receptor and Chemokine Receptor on Intraedidermal T Cells in Psoriasis Vulgaris", Clinical and Experimental Dermatology, vol. 29, No. 6, Nov. 1, 2004, 658-663.

Tylaska, "CCR2 Regulates the Level of MCP-1/CCL2 in Vitro and at Inflammatory Sites and Controls T Cell Activation in Response to Alloantigen", Cytokine, vol. 18, No. 4, May 1, 2002, 184-190.

Vergunst, et al., "Modulation of CCR2 in Rheumatoid Arthritis—A Double-Blind, Randomized, Placebo-Controlled Clinical Trial", Arthritis & Rheumatism, vol. 58, No. 7, Jul. 1, 2008, 1931-1939.

Vita, et al., "Synthesis and Characterization of Biologically Functional Biotinylated RANTES", Journal of Immunological Methods, Aug. 1, 2002, 53-65.

Walters, et al., "Characterization of CCX282-B, and Orally Bioavailable Antagonist of the CCR9 Chemokine Receptor, for Treatment of Inflammatory Bowel Disease", Journal of Pharmacology and Experimental Therapeutics, vol. 335, No. 1, Oct. 1, 2010, 61-69.

Williams, et al., "Eotaxin and CCR3 as Therapeutic Targets in Asthma and Allergy", Chemokines 2, retrieved from the Internet on Sep. 17, 2012: http://www.pasteur.fr/applications/euroconf/chemokines2/Williams.pdf Jan. 1, 2003, 4.

Yawalkar, et al., "Enhanced Expression of Eotaxin and CCR3 in Atopic Dermatitis", Journal of Investigative Dermatology, vol. 113, No. 1, Jul. 1, 1999, 43-48.

Hasegawa et al., "Increased chemokine receptor CCR7/EB11 expression enhances the infiltration of lymphoid organs by adult T-cell leukemia cells," Blood, 2000, 95(1):30-38.

Lazennec et al., "Chemokines and chemokine receptors: new insights into cancer-related inflammation," Trends in Molecular Medicine, 2010, 16(3):133-144.

Yan et al., "Expression of vascular endothelial growth factor C and chemokine receptor CCR7 in gastric carcinoma and their values in predicting lymph node metastasis," World J Gastroenterol, 2004, 10(6):783-790.

European Patent Office Action for Application No. 12727916.4 dated Apr. 19, 2018 (7 pages).

Sonnleitner, "Adipositas: Inflammation im viszeralen Fettgewebe" Dissertation, University Hospital Ulm Center for Internal Medicine Department of Internal Medicine II, 2010.

Stulnig, "Adipositas und die Entziindung des Fettgewebes," Journal für Klinische Endokrinologie und Stoffwechsel—Austrian, 2009, 2(3):17-21.

European Patent Office Action for Application No. 12727914.9 dated Feb. 19, 2018 (7 pages).

Palchevskiy et al., "Immune response CC chemokinesCCL2 and CCL5 are associated with pulmonary sarcoidosis," Fibrogenesis & Tissue Repair, 2011, 4:10, 12 pages.

Kerstjens et al., "Tolerability and efficacy of inhaled AZD4818, a CCR1 antagonist, in moderate to severe COPD patients," Respiratory Medicine, 2010, 104, pp. 1297-1303.

Alfonso-Perez et al., "Anti-CCR7 monoclonal antibodies as a novel tool for the treatment of chronic lymphocyte leukemia," J. Leukoc. Biol., 2006, 79:1157-1165.

Cummings et al., "Expression and Function of the Chemokine Receptors CXCR1 and CXCR2 in Sepsis," J. Immunology, 1999, 162: 2341-2346.

Kanamori et al., "Inhibition of MCP-1/CCR2 pathway ameliorates the development of diabetic nephropathy," Biochemical and Biophysical Research Communications, 2007, 360: 772-777.

Kaneider et al., "Reversing Systemic inflammatory Response syndrome with chemokine receptor pepducins," Nature Medicine, 2005, 11: 661-665.

Lopez-Giral et al., "Chemokine receptors that mediate B cell homing to secondary lymphoid tissues are highly expressed in B cell chronic lymphocytic leukemia and non-Hodgkin lymphomas with widespread nodular dissemination," J. Leukoc. Biol., 2004, 46:462-471.

NCI Dictionary of Cancer Terms, downloaded Sep. 27, 2018.

Owen, "Chemokine Receptors in Airway Disease: Which Receptors to Target?," Pulmonary Pharm and Therap, 2001, 14: 193-202.

Stuart et al., "Chemokines and chemokine receptors in mood disorders, schizophrenia, and cognitive impairment: A systematic review of biomarker studies," Neuroscience and Behavioral Review, 2014, 42:93-115.

Stuart et al., "Systematic review of the neurobiological relevance of chemokines to psychiatric disorders," Frontiers in Cellular Neuroscience, 2015, 9:1-15.

Tamura et al., "C-C chemokine receptor 2 inhibitor improves diet-induced development of insulin resistance and hepatic steatosis in mice," J Atheroscler Thromb., 2010, 17: 219-228.

Tamura et al., "Inhibition of CCR2 Ameliorates Insulin Resistance and Hepatic Steatosis in db/db Mice," Arterioscler Thromb Vasc Biol., 2008, 28: 2195-2201.

Till et al., "The chemokine receptor CCR7 and α4 integrin are important for migration of chronic lymphocytic leukemia cells into lymph nodes," Blood, 2002, 99:2977-2984.

(56) References Cited

OTHER PUBLICATIONS

Zaballos et al., "Cutting Edge: Identification of the Orphan Chemokine Receptor GPR-9-6 as CCR9, the Receptor for the Chemokine TECK," J. Immunol., 1999, 162:5671-5675.
United States Patent Office Action for U.S. Appl. No. 15/629,691 dated Dec. 17, 2018 (9 pages).
United States Patent Office Action for U.S. Appl. No. 15/629,700 dated Oct. 2, 2018 (11 pages).
United States Patent Office Action for U.S. Appl. No. 15/629,705 dated Dec. 3, 2018 (10 pages).
United States Patent Office Action for U.S. Appl. No. 15/629,708 dated Oct. 17, 2018 (13 pages).
United States Patent Office Action for U.S. Appl. No. 15/629,713 dated Oct. 26, 2018 (12 pages).
Mine et al., "Increased expression levels of monocyte CCR2 and monocyte chemoattractant protein-1 in patients with diabetes mellitus," Biochemical and Biophysical Communications, 2006, 344: 780-785.
United States Patent Office Notice of Allowance for U.S. Appl. No. 15/629,700 dated May 9, 2019 (9 pages).
United States Patent Office Corrected Notice of Allowability for U.S. Appl. No. 15/629,708 dated May 10, 2019 (5 pages).
United States Patent Office Notice of Allowance for U.S. Appl. No. 15/629,713 dated Apr. 29, 2019 (8 pages).
United States Patent Office Notice of Allowance for U.S. Appl. No. 15/629,705 dated May 24, 2019 (8 pages).
United States Patent Office Notice of Allowance for U.S. Appl. No. 15/629,708 dated Apr. 15, 2019 (10 pages).
United States Patent Office Notice of Allowance for U.S. Appl. No. 15/629,691 dated Jun. 14, 2019 (9 pages).

\* cited by examiner ulimit -t 30; /usr/molbio/bin/lalign -f -14 -g -4 -K 3 ./wwwtmp/.11134.1.seq ./wwwtmp/.11134.2.seq > ./wwwtmp/.11134.out LALIGN finds the best local alignments between two sequences version 2.1u09 December 2006 Please cite: X. Huang and W. Miller (1991) Adv. Appl. Math. 12:373-381 alignments < E( 0.05):score: 38 (3 max)

```
Comparison of:
(A) ./wwwtmp/.11134.1.seq MCP1 (human) 76 bp
 - 76 aa
(B) ./wwwtmp/.11134.2.seq MCP-5 (mouse) 82 bp
 - 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1     PDAINAPVTCCYNFTNRKISVQRLASYRRITSSKCPKEAVIFKTIVAKEICADPKQKWVQ
         :::...::::::::  ...:: :...: :::::::::.::.::::::.::. :::::::::..:::.
MCP-5    PDAVSTPVTCCYNVVKQKIHVRKLKSYRRITSSQCPREAVIFRTILDKEICADPKEKWVK
              10        20        30        40        50        60

70
MCP1     DSMDHLDKQTQTPKT
         .:..::::  .::
MCP-5    NSINHLDKTSQTFILEPSCLG
              70
```

*FIG. 10*

H-GPDAVSTPVTCCYNVVKQKIHVRKLKSYRRITSSQ
CPREAVIFRTILDKEICADPKEKWVKNSINHLDKTSQTFKL-CONH$_2$

H$_2$N-SPYSSDTTPCCFAYIARPLPRAHIKEYFYTSGKCSNP
AVVFVTRKNRQVCANPEKKWVREYINSLEKS-CO$_2$H

SEQUENCE LISTING

```
<160> NUMBER OF SEQ ID NOS: 31

<210> SEQ ID NO 1
<211> LENGTH: 99
<212> TYPE: PRT
<213> ORGANISM: Artificial sequence
<220> FEATURE:
<223> OTHER INFORMATION: Synthesised peptide

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 76
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (64)..(64)
<223> OTHER INFORMATION: X = Met or Nleu
```

```
<400> SEQUENCE: 2

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Xaa
    50                  55                  60

Asp His Leu Asp Lys Gln Thr Gln Thr Pro Lys Thr
65                  70                  75

<210> SEQ ID NO 3
<211> LENGTH: 68
<212> TYPE: PRT
<213> ORGANISM: Artificial sequence
<220> FEATURE:
<223> OTHER INFORMATION: Synthesised peptide

<400> SEQUENCE: 3

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65

<210> SEQ ID NO 4
<211> LENGTH: 104
<212> TYPE: PRT
<213> ORGANISM: Artificial sequence
<220> FEATURE:
<223> OTHER INFORMATION: Synthesised peptide

<400> SEQUENCE: 4

Met Lys Ile Ser Thr Leu Leu Cys Leu Leu Leu Ile Ala Thr Thr Ile
1               5                   10                  15

Ser Pro Gln Val Leu Ala Gly Pro Asp Ala Val Ser Thr Pro Val Thr
            20                  25                  30

Cys Cys Tyr Asn Val Val Lys Gln Lys Ile His Val Arg Lys Leu Lys
        35                  40                  45

Ser Tyr Arg Arg Ile Thr Ser Ser Gln Cys Pro Arg Glu Ala Val Ile
    50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100

<210> SEQ ID NO 5
<211> LENGTH: 82
<212> TYPE: PRT
<213> ORGANISM: Artificial sequence
```

<220> FEATURE:
<223> OTHER INFORMATION: Synthesised peptide

<400> SEQUENCE: 5

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly

<210> SEQ ID NO 6
<211> LENGTH: 76
<212> TYPE: PRT
<213> ORGANISM: Artificial sequence
<220> FEATURE:
<223> OTHER INFORMATION: Synthesised peptide

<400> SEQUENCE: 6

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu
65                  70                  75

<210> SEQ ID NO 7
<211> LENGTH: 76
<212> TYPE: PRT
<213> ORGANISM: Artificial sequence
<220> FEATURE:
<223> OTHER INFORMATION: Synthesised peptide

<400> SEQUENCE: 7

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Lys Leu
65                  70                  75

<210> SEQ ID NO 8
<211> LENGTH: 76
<212> TYPE: PRT
<213> ORGANISM: Artificial sequence
<220> FEATURE:
<223> OTHER INFORMATION: Synthesised peptide

```
<220> FEATURE:
<221> NAME/KEY: X
<222> LOCATION: (1)..(1)
<223> OTHER INFORMATION: X = pyroGlu

<400> SEQUENCE: 8

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 9
<211> LENGTH: 76
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is K(ivDde)

<400> SEQUENCE: 9

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Xaa Thr
65                  70                  75

<210> SEQ ID NO 10
<211> LENGTH: 76
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)
```

```
<400> SEQUENCE: 10

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 11
<211> LENGTH: 76
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu

<400> SEQUENCE: 11

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 12
<211> LENGTH: 76
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is K(ivDde)

<400> SEQUENCE: 12

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75
```

<210> SEQ ID NO 13
<211> LENGTH: 76
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 13

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 14
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 14

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 15
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (73)..(73)
<223> OTHER INFORMATION: X is K(ivDde)

<400> SEQUENCE: 15

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
        50                  55                  60

Leu Asp Gln Lys Ser Pro Thr Pro Xaa Pro
65                  70

<210> SEQ ID NO 16
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (73)..(73)
<223> OTHER INFORMATION: X is K(PEG-Biotin)

<400> SEQUENCE: 16

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
        50                  55                  60

Leu Asp Gln Lys Ser Pro Thr Pro Xaa Pro
65                  70

<210> SEQ ID NO 17
<211> LENGTH: 68
<212> TYPE: PRT
<213> ORGANISM: Artificial sequence
<220> FEATURE:
<223> OTHER INFORMATION: Synthesised peptide

<400> SEQUENCE: 17

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Lys Ser
65

<210> SEQ ID NO 18
<211> LENGTH: 68
<212> TYPE: PRT
<213> ORGANISM: Artificial sequence
<220> FEATURE:
<223> OTHER INFORMATION: Synthesised peptide

```
-continued

<220> FEATURE:
<221> NAME/KEY: X
<222> LOCATION: (67)..(67)
<223> OTHER INFORMATION: X is K(ivDde)

<400> SEQUENCE: 18

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 19
<211> LENGTH: 68
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 19

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 20
<211> LENGTH: 70
<212> TYPE: PRT
<213> ORGANISM: Artificial sequence
<220> FEATURE:
<223> OTHER INFORMATION: Synthesised peptide

<400> SEQUENCE: 20

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70
```

```
<210> SEQ ID NO 21
<211> LENGTH: 70
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (68)..(68)
<223> OTHER INFORMATION: X is K(ivDde)

<400> SEQUENCE: 21

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 22
<211> LENGTH: 70
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (68)..(68)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 22

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 23
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
```

<400> SEQUENCE: 23

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Lys Val Phe
65                  70

<210> SEQ ID NO 24
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 24

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 25
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 25

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 26
<211> LENGTH: 73
<212> TYPE: PRT
<213> ORGANISM: Artificial sequence
<220> FEATURE:
<223> OTHER INFORMATION: Synthesised peptide

<400> SEQUENCE: 26

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 27
<211> LENGTH: 74
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (74)..(74)
<223> OTHER INFORMATION: X is PEG-K(ivDde)

<400> SEQUENCE: 27

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 28
<211> LENGTH: 74
<212> TYPE: PRT
<213> ORGANISM: Artificial sequence
<220> FEATURE:
<223> OTHER INFORMATION: Synthesised peptide

```
<220> FEATURE:
<221> NAME/KEY: X
<222> LOCATION: (74)..(74)
<223> OTHER INFORMATION: X = residue that can be biotinylated, e.g.
      lysine, ornithine or diaminopropionic acid and optionally is
      biotinylated, optionally via a spacer molecule such as PEG, e.g.
      K(PEG-Biotin) and may be attached via a spacer molecule, e.g.PEG-
      K(Biotin)

<400> SEQUENCE: 28

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 29
<211> LENGTH: 77
<212> TYPE: PRT
<213> ORGANISM: Artificial sequence
<220> FEATURE:
<223> OTHER INFORMATION: Synthesised peptide

<400> SEQUENCE: 29

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 30
<211> LENGTH: 78
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (77)..(77)
<223> OTHER INFORMATION: X is K(ivDde), optionally attached via a spacer
      such as PEG, e.g. -PEG-K(ivDde)
<220> FEATURE:
<221> NAME/KEY: misc_feature
<222> LOCATION: (78)..(78)
<223> OTHER INFORMATION: Xaa can be any naturally occurring amino acid

<400> SEQUENCE: 30

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45
```

```
Gly Glu Lys Arg Cys Leu Asn Pro Glu Ser Lys Ala Ile Lys Asn Leu
 50                  55                  60

Leu Lys Ala Val Ser Lys Glu Arg Ser Lys Arg Ser Pro Xaa
 65                  70                  75

<210> SEQ ID NO 31
<211> LENGTH: 78
<212> TYPE: PRT
<213> ORGANISM: Artificial sequence
<220> FEATURE:
<223> OTHER INFORMATION: Synthesised peptide
<220> FEATURE:
<221> NAME/KEY: X
<222> LOCATION: (77)..(77)
<223> OTHER INFORMATION: X = residue that can be biotinylated, e.g.
      lysine, ornithine or diaminopropionic acid and optionally is
      biotinylated, optionally via a spacer molecule such as PEG, e.g.
      K(PEG-Biotin) and may be attached via a spacer molecule, e.g.PEG-
      K(Biotin)
<220> FEATURE:
<221> NAME/KEY: misc_feature
<222> LOCATION: (78)..(78)
<223> OTHER INFORMATION: Xaa can be any naturally occurring amino acid

<400> SEQUENCE: 31

Val Pro Leu Ser Arg Thr Val Arg Cys Thr Cys Ile Ser Ile Ser Asn
 1               5                  10                  15

Gln Pro Val Asn Pro Arg Ser Leu Glu Lys Leu Glu Ile Ile Pro Ala
                 20                  25                  30

Ser Gln Phe Cys Pro Arg Val Glu Ile Ile Ala Thr Met Lys Lys Lys
             35                  40                  45

Gly Glu Lys Arg Cys Leu Asn Pro Glu Ser Lys Ala Ile Lys Asn Leu
 50                  55                  60

Leu Lys Ala Val Ser Lys Glu Arg Ser Lys Arg Ser Pro Xaa
 65                  70                  75
```

TREATING MULTIPLE SCLEROSIS

CROSS-REFERENCE TO RELATED APPLICATION(S)

This application is a divisional of U.S. patent application Ser. No. 14/105,628, filed on Dec. 13, 2013, now issued as U.S. Pat. No. 9,726,666, which is a continuation-in-part of International Patent Application No. PCT/GB2012/051357, filed on Jun. 13, 2012, which claims priority to U.S. Provisional Patent Application No. 61/496,442, filed on Jun. 13, 2011. U.S. patent application Ser. No. 14/105,628 is also a continuation-in-part of International Patent Application No. PCT/GB2012/051349, filed on Jun. 13, 2012, which claims priority to U.S. Provisional Patent Application No. 61/496,167, filed on Jun. 13, 2011. U.S. patent application Ser. No. 14/105,628 is also a continuation-in-part of International Patent Application No. PCT/GB2012/051348, filed on Jun. 13, 2012, which claims priority to U.S. Provisional Patent Application No. 61/496,288, filed on Jun. 13, 2011. U.S. patent application Ser. No. 14/105,628 is also a continuation-in-part of International Patent Application No. PCT/GB2012/051351, filed on Jun. 13, 2012, which claims priority to U.S. Provisional Patent Application No. 61/496,242, filed on Jun. 13, 2011. U.S. patent application Ser. No. 14/105,628 is also a continuation-in-part of International Patent Application No. PCT/GB2012/051350, filed on Jun. 13, 2012, which claims priority to U.S. Provisional Patent Application No. 61/496,209, filed on Jun. 13, 2011. U.S. patent application Ser. No. 14/105,628 is also a continuation-in-part of International Patent Application No. PCT/GB2012/051355, filed on Jun. 13, 2012, which claims priority to U.S. Provisional Patent Application No. 61/496,195, filed on Jun. 13, 2011. U.S. patent application Ser. No. 14/105,628 is also a continuation-in-part of International Patent Application No. PCT/GB2012/051345, filed on Jun. 13, 2012, which claims priority to U.S. Provisional Patent Application No. 61/496,228, filed on Jun. 13, 2011. U.S. patent application Ser. No. 14/105,628 is also a continuation-in-part of International Patent Application No. PCT/GB2012/051352, filed on Jun. 13, 2012, which claims priority to U.S. Provisional Patent Application No. 61/496,264, filed on Jun. 13, 2011. U.S. patent application Ser. No. 14/105,628 is also a continuation-in-part of International Patent Application No. PCT/GB2012/051346, filed on Jun. 13, 2012, which claims priority to U.S. Provisional Patent Application No. 61/496,184, filed on Jun. 13, 2011. U.S. patent application Ser. No. 14/105,628 is also a continuation-in-part of International Patent Application No. PCT/GB2012/051353, filed on Jun. 13, 2012, which claims priority to U.S. Provisional Patent Application No. 61/496,329, filed on Jun. 13, 2011. U.S. patent application Ser. No. 14/105,628 is also a continuation-in-part of International Patent Application No. PCT/GB2012/051356, filed on Jun. 13, 2012, which claims priority to U.S. Provisional Patent Application No. 61/496,377, filed on Jun. 13, 2011. U.S. patent application Ser. No. 14/105,628 is also a continuation-in-part of International Patent Application No. PCT/GB2012/051354, filed on Jun. 13, 2012, which claims priority to U.S. Provisional Patent Application No. 61/496,352, filed on Jun. 13, 2011. The entire contents of each of these applications are fully incorporated herein by reference.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 21, 2017, is named P81602725US00-211226-9002-US01-SEQ-LIST-06-21-17.txt, and is 27,709 bytes in size.

FIELD OF THE INVENTION

The various embodiments of the present invention relates to products for and methods of treating inflammatory conditions, such as multiple sclerosis, in particular active and stable relapsing-remitting multiple sclerosis, primary progressive, secondary progressive and progressive relapsing multiple sclerosis. Companion diagnostics are also described.

BACKGROUND OF THE INVENTION

Multiple sclerosis is a neurodegenerative disease affecting the central nervous system (CNS). Disease onset usually occurs in young adults between the ages of 20 and 40, however, the precise underlying cause of MS is unknown. There is currently no cure for this disabling disease and treatment is primarily focussed on management of symptoms.

Irrespective of disease etiology, the immune system has been found to play a central role in the pathogenesis of MS. In particular, the lesions that develop in the brain and/or spinal cord during disease progression are frequently characterised by an excessive inflammatory infiltrate and the presence of autoreactive CD4+/CD8+ T cells and autoreactive B cells. Furthermore, ongoing assault of the CNS mediated by a variety of inflammatory and/or immune cell types appears to be the primary cause of the nerve damage and in particular, the axon demyelination, associated with this disease.

Apheresis is a treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. WO2010/029317 describes apheresis columns useful for treating inflammatory conditions including a chemokine immobilised on a solid support.

SUMMARY OF THE INVENTION

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of multiple sclerosis. In particular, various types of multiple sclerosis, such as active and stable relapsing-remitting multiple sclerosis include an inflammatory component. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects suffering from MS exhibit increased frequency of chemokine receptor expressing cells in the peripheral blood, in particular CCR2 and CCR6 expressing T lymphocytes, compared to healthy controls. It is also shown herein that the CCR2 cells can be removed using a suitable binding reagent, in particular MCP-1 (in biotinylated form) immobilized on a suitable matrix. Similarly, it is shown herein that (the additional) CCR6-expressing cells can be depleted using a suitable binding reagent, in particular CCL20 (MIP-31), in biotinylated form, immobilized on a suitable matrix.

Thus, in certain embodiments the invention serves to reduce the recruitment of inflammatory leukocytes, which express characteristic chemokine receptors, and possibly express characteristic chemokine receptors at increased levels, to sites of inflammation linked to multiple sclerosis such as active and stable relapsing-remitting multiple sclerosis, primary progressive, secondary progressive and progressive relapsing multiple sclerosis. This is achieved using specific binding reagents to capture specific chemokine receptor-expressing inflammatory leukocytes from the patient. Accordingly, in certain embodiments the invention provides in a first aspect a method for treating multiple sclerosis comprising applying peripheral blood from a patient to an apheresis column loaded with a solid support comprising one or more binding reagents capable of specifically binding to one or more chemokine receptors, in particular to the chemokine receptors selected from CCR2, CCR6, CCR3, CCR5, CCR1, CXCR3 and/or CCR9, immobilized directly or indirectly on the support thus removing chemokine receptor, in particular one or more of CCR2, CCR6, CCR3, CCR5, CCR1, CXCR3 and/or CCR9, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of $CCR2^{hi}$, $CCR6^{hi}$, $CCR3^{hi}$, $CCR5^{hi}$, $CCR1^{hi}$, $CXCR3^{hi}$ and/or $CCR9^{hi}$ cells as defined herein for removal from the peripheral blood. "High" expression may be determined according to standard flow cytometry techniques. The level is measured relative to levels of expression of the chemokine receptor in cells taken from a healthy subject. The attached FIG. 13 provides an example of a gating strategy.

In other embodiments the invention further provides a binding reagent capable of specifically binding to one or more chemokine receptors, in particular to a chemokine receptor selected from CCR2, CCR6, CCR3, CCR5, CCR1, CXCR3 and/or CCR9, for use in the treatment of multiple sclerosis, wherein the one or more binding reagents is immobilized, directly or indirectly, on a solid support contained within an apheresis column, to which is applied peripheral blood from a patient thus removing one or more chemokine receptor/CCR2, CCR6, CCR3, CCR5, CCR1, CXCR3 and/or CCR9 expressing cells from the peripheral blood of the patient. In certain embodiments the invention also provides for use of one or more binding reagents capable of specifically binding to a chemokine receptor/the chemokine receptor CCR2, CCR6, CCR3, CCR5, CCR1, CXCR3 and/or CCR9 for use in the manufacture of an apheresis column for treatment of multiple sclerosis, wherein the one or more binding reagents is immobilized on a solid support contained within the apheresis column, to which is applied peripheral blood from a patient thus removing one or more chemokine receptor/CCR2, CCR6, CCR3, CCR5, CCR1, CXCR3 and/or CCR9 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat multiple sclerosis. By treatment is meant a reduction in the specific chemokine receptor expressing cells in the peripheral blood of the patient. The reduction may comprise a reduction in cells that express chemokine receptors, in particular one or more of CCR2, CCR6, CCR3, CCR5, CCR1, CXCR3 and/or CCR9, at increased levels in diseased patients. The patient is typically a human patient but the term patient may include both human and non-human animal subjects in some embodiments. In the context of the various embodiments of the present invention, this typically involves a reduction in one or more of CCR2, CCR6, CCR3, CCR5, CCR1, CXCR3 and/or CCR9 expressing cells, such as one or more of "$CCR2^{hi}$, $CCR6^{hi}$, $CCR3^{hi}$, $CCR5^{hi}$, $CCR1^{hi}$, $CXCR3^{hi}$ and/or $CCR9^{hi}$" expressing cells, in the peripheral blood of the patient. The CCR2, CCR6, CCR3, CCR5, CCR1, CXCR3 and/or CCR9 expressing cells comprise, consist essentially of or consist of monocytes, lymphocytes, neutrophils, macrophages, eosinophils and basophils, in certain embodiments. In specific embodiments the cells removed in order to treat MS comprise T lymphocytes, in particular CCR2 and/or CCR6 expressing T lymphocytes.

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++ CD16– monocyte). Non-classical monocytes may be characterized by low level expression of CD14 and with additional co-expression of the CD16 receptor (CD14+ CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of $CD16^+CD32^+CD64^+$ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of $SRA/B^+CD163^+MR^+CD14^+$ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where $CD14^+CD16^-CXC3R1^{low}$ monocytes are considered the "inflammatory" subset and the $CD14^{low}CD16^+CXC3R1^{high}$ are "resident" monocytes.

The three major types of lymphocyte are T cells, B cells and natural killer (NK) cells. The term "T-lymphocyte" includes $CD4^+$ T cells such as T helper cells (Th1 cells and Th2 cells), and $CD8^+$ T cells such as cytotoxic T cells. Th1 cells may be characterized by expression of CCR5 and/or by production of IFN-γ. Th2 cells may be characterized by expression of CCR3 and/or by production of IL-4.

The claimed methods may target eosinophils. The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125.

Basophils may also be known as basophil granulocyte. In contrast to eosinophils, these leukocytes are basophilic, i.e., they are susceptible to staining by basic dyes. Basophils contain large cytoplasmic granules which obscure the cell nucleus under the microscope. However, when unstained, the nucleus is visible and it usually has 2 lobes. Basophils store histamine, which is secreted by the cells upon stimulation.

Basophils have protein receptors on their cell surface that bind IgE, an immunoglobulin involved in macroparasite defense and allergy. It is the bound IgE antibody that confers a selective response of these cells to environmental substances, for example, pollen proteins or helminth antigens. Recent studies in mice suggest that basophils may also regulate the behavior of T cells and mediate the magnitude of the secondary immune response. Basophils may display an immunophenotype based upon expression (or lack thereof, indicated as "+" or "−" respectively of one or more of the following markers: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, αβTCR−, α4 and β4-integrin negative.

When activated, basophils degranulate to release histamine, proteoglycans (e.g. heparin and chondroitin), and proteolytic enzymes (e.g. elastase and lysophospholipase). They also secrete lipid mediators like leukotrienes, and several cytokines. Histamine and proteoglycans are pre-stored in the cell's granules while the other secreted substances are newly generated. Each of these substances contributes to inflammation. Recent evidence suggests that basophils are an important source of the cytokine, interleukin-4, perhaps more important than T cells. Interleukin-4 is considered one of the critical cytokines in the development of allergies and the production of IgE antibody by the immune system. There are other substances that can activate basophils to secrete which suggests that these cells have other roles in inflammation.

The various embodiments of the methods of the invention may involve specific binding interactions with any one or more of these further cell-surface (and cell-specific) markers in addition to the removal based upon binding to CCR2, CCR6, CCR3, CCR5, CCR1, CXCR3 and/or CCR9. Suitable binding reagents can be prepared to specifically bind to these cell-surface markers. The discussion of CCR2, CCR6, CCR3, CCR5, CCR1, CXCR3 and/or CCR9 specific binding reagents thus applies mutatis mutandis.

CCR2, CCR6, CCR3, CCR5, CCR1, CXCR3 and/or CCR9 expressed on these aforementioned cells are bound by chemokines such as monocyte chemoattractant protein-1 (MCP-1), MCP-2, MCP-3, MCP-4, MCP-5, MIP-3alpha, MIG (CXCL9), IP10 (CXCL10), CXCL11 (I-TAC) and RANTES. Eotaxin (aka CCL11 binds CCR3 only), eotaxin-2 (aka CCL24 binds CCR3 only), eotaxin-3 (aka CCL26 binds CCR3 only), RANTES (CCL5 is promiscuous CCR1, CCR3, CCR5), MCP-2, (aka CCL8 is promiscuous) MCP-3 (aka CCL7 is promiscuous), MCP-4 (aka CCL13 is promiscuous), MIP-1a (aka CCL3 promiscuous CCR1, CCR3, CCR5), MEC (CCL28 binds CCR3 and CCR10), HCC-2 (CCL15 binds CCR1 and CCR3). Chemokines MIP1γ (CCL9), MRP-2 (CCL10), MIp-1δ (CCL15) and CCL23 appear to bind CCR1 only, Chemokines Eotaxin, Eotaxin-2 only bind CCR3, Chemokine MIP1β (CCL4) only binds CCR5. MCP-5 binds CCR2 only.

MCP-1 (CCL2) is a major chemoattractant for monocytes and memory T cells by means of their binding to its specific cell-surface receptor, CC-chemokine receptor-2 (CCR2). CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302 and MCP-1-R. The NCBI Reference Sequence is NM_001123041.2 as available on 13 Jun. 2011, which is incorporated herein by reference in its entirety.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1aR. The Entrez Gene reference sequence for CCR1 is 1230 as available on 13 Jun. 2011, which is incorporated herein by reference in its entirety.

CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CCR6 is the gene symbol approved by the HUGO Gene Nomenclature Committee for chemokine (C—C motif) receptor 6. The HGNC ID for this gene is 1607. The gene is located at chromosome position 6q27. The previous symbol and name for the gene is STRL22. Synonyms for this gene include BN-1, CD196, CKR-L3, CMKBR6, DCR2, DRY-6, GPR-CY4, GPR29. The Genbank reference sequence for CCR6 is U68030.1 as available on 13 Jun. 2011, which is incorporated herein by reference in its entirety.

CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CXCR3 is the gene symbol approved by the HUGO Gene Nomenclature Committee for chemokine (C—X—C motif) receptor 3. The HGNC ID for this gene is 4540. The gene is located at chromosome position Xq13. The previous symbol and name for the gene is "G protein-coupled receptor 9", GPR9. Synonyms for this gene include CD183, CKR-L2, CMKAR3, IP10-R and MigR. The Genbank reference sequence for CXCR3 is U32674.1 as available on 13 Jun. 2011, which is incorporated herein by reference in its entirety.

Treatment according to the various embodiments of the invention may result in alleviation or amelioration of symptoms, prevention of progression, regression of the condition, or complete recovery. Measurable parameters of successful treatment include one or more, up to all, of Multiple Sclerosis Severity Score or MRI. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR2, CCR6, CCR3, CCR5, CCR1, CXCR3 and/or CCR9, expressing cells from the peripheral blood of the patient. In specific embodiments, at least around 50% depletion is achieved in a single treatment. Thus, successful treatment may be defined with reference to depletion of one or more of CCR2, CCR6, CCR3, CCR5, CCR1, CXCR3 and/or CCR9 expressing cells. Treatment may lead to depletion of between approximately 100 and 500 million CCR2, CCR6, CCR3, CCR5, CCR1 and/or CCR9 expressing cells, such as monocytes, in certain embodiments and more particularly to about 100, 150, 200, 250, 300, 350, 400, 450, or 500 million CCR2, CCR6, CCR3, CCR5, CCR1 and/or CCR9 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR2, CCR6, CCR3, CCR5, CCR1, CXCR3 and/or CCR9 expressing cells, such as a 50% reduction in one or more of CCR2, CCR6, CCR3, CCR5, CCR1, CXCR3 and/or CCR9 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR2, CCR6, CCR3, CCR5, CCR1, CXCR3 and/or CCR9. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR2, CCR6, CCR3, CCR5, CCR1, CXCR3 and/or CCR9 from the peripheral blood. Whilst it is not precluded that the binding reagent is capable of binding to other molecules, such as other chemokine receptors, the binding reagent will preferentially bind to cells expressing one or more of CCR2, CCR6, CCR3, CCR5, CCR1, CXCR3 and/or CCR9 and in particular to cells expressing increased levels of one or more of CCR2, CCR6, CCR3, CCR5, CCR1, CXCR3 and/or CCR9 (as defined further herein). The binding reagent capable of specifically binding to CCR2, CCR6, CCR3, CCR5, CCR1, CXCR3 and/or CCR9 may be either an agonist or an antagonist of CCR2, CCR6, CCR3, CCR5, CCR1, CXCR3 and/or CCR9. As the disease condition relies upon up-regulation of expression of or signaling via CCR2, CCR6, CCR3, CCR5, CCR1, CXCR3 and/or CCR9, in certain embodiments the binding reagent capable of specifically binding to CCR2, CCR6, CCR3, CCR5, CCR1, CXCR3 and/or CCR9 is an antagonist of CCR2, CCR6, CCR3, CCR5, CCR1, CXCR3 and/or CCR9., respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19(3): 295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of various embodiments of the the invention). The chemokine does not necessarily need to retain biological activity as it is specific binding affinity for CCR2, CCR6, CCR3, CCR5, CCR1, CXCR3 and/or CCR9 that is required. In certain embodiments, the chemokine lacks biological activity, for example in terms of activation of the (CCR2, CCR6, CCR3, CCR5, CCR1, CXCR3 and/or CCR9) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques $2^{nd}$ edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the $1^{st}$ and $3^{rd}$ and $2^{nd}$ and $4^{th}$ cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention include MCP-1, MCP-2, MCP-3, MCP-4, MCP-5, MIP-3alpha, MIG (CXCL9), IP10 (CXCL10), CXCL11 (I-TAC), CCL25 and RANTES. Both MCP-1 and MCP-5 bind solely to the chemokine receptor CCR2 and so these chemokines may be preferred in some embodiments. Each chemokine is able to bind to a chemokine receptor implicated in multiple sclerosis.

The modified and truncated chemokines described in greater detail herein (with reference to the relevant amino acid sequences, as set forth in the SEQ ID NOs and accompanying experimental examples) may each be applied according to the present invention. Such modified forms may instruct the skilled person regarding additional modified forms of the same and other chemokines which may be suitable for use in the invention. Chemokines show variable sequence homology varying from less than 20% to over 90% but all share very similar tertiary structures consisting of a disordered N-terminus, followed by a long loop (the N-loop) that ends in a $3_{10}$ helix, a 3-stranded β-sheet and a C-terminal helix. The overall topology is stabilsed by disulphide bonds. This common tertiary structure is a common feature of the chemokine protein family (Fernandez E J and Lolis E., Annu. Rev. Pharmacol. Toxicol., 202, 42, 469-99; Allen S J et al, Annu. Rev. Immunol., 2007, 25, 787-820, incorporated herein by reference).

Truncations within this N-terminal region can maintain binding to the receptor but can lead to a change or loss of function (for examples Zhang Y J et al, J. Biol. Chem., 1994, 269, 15918; Gong J-H and Clark-Lewis I., *J. Exp. Med.*, 1995, 181, 631-640; Fernandez E J and Lolis E., Annu. Rev. Pharmacol. Toxicol., 202, 42, 469-99; Allen S J et al, Annu. Rev. Immunol., 2007, 25, 787-820, each of which is incorporated herein by reference).

Truncations at the C-terminus of the chemokine can also be made and maintain receptor binding activity (Treating Inflammatory Disorders, Ola Winqvist and Graham Cotton, WO2010/029317, incorporated herein by reference in its entirety).

In other embodiments, fragments and variants of chemokines are used in the devices and methods as disclosed herein. More particularly, such fragments and variants retain the ability to specifically bind to their cognate chemokine receptor. Chemokines are known by those skilled in the art to share specific receptor binding domains, including a similar monomeric fold, characterized, for example, by a disordered amino-terminal domain, followed by a conserved core region, consisting of the so called "N-loop," three anti-parallel β-strands, and a carboxyl-terminal α-helix. While not being bound by theory, it is believed that the chemokine-chemokine receptor interaction is a two-step mechanism, in which the core of the chemokine interacts first with a binding site formed by the extracellular domains of the receptor, while another interaction is formed between the chemokine N terminus and a second binding site on the receptor in order to trigger receptor activation. Thus, a "fragment," such as a functional fragment of a chemokine is intended to mean a portion of the amino acid sequence of the protein that retains binding for its cognate receptor. The fragment may include, for example, the monomeric fold region, or portions thereof such as the amino-terminal domain, the conserved core region and/or the "N-loop," the anti-parallel β-strands, and/or the carboxyl-terminal α-helix or combinations and portions thereof.

Further, it is recognized that a polypeptide can be considerably mutated without materially altering one or more of the polypeptide's functions, for example, without altering specific binding and/or the folding of the protein. The genetic code is well known to be degenerate, and thus different codons encode the same amino acids. Even where an amino acid substitution is introduced, the mutation can be conservative and have no material impact on the essential functions of a protein (see for example, Stryer, Biochemistry 4th Ed., W. Freeman & Co., New York, N.Y., 1995). This includes, for example, the ability of the protein to bind and interact with other proteins, such as a truncated chemokine binding to its cognate receptor.

In some examples, part of a polypeptide chain can be deleted without impairing or eliminating all of its functions. For example, the deletion of between about 1 and about 20 amino acids on the C- and/or N-terminus, such as deletions of about 1, 2, 3, 4, 5, 6, 7, 8, 9, 10, 11, 12, 13, 14, 15, 16, 17, 18, 19, or 20 amino acids at the C- and/or N-terminus, can result in a chemokine that retains function, such as specific binding of its cognate receptor. Such truncations can retain the full function of an entire protein, and/or can allow for retained functions such as protein-protein interactions as in the case of ligand-receptor interactions. Chemokines having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type chemokine can also be used in the methods and devices disclosed herein. Moreover, insertions or additions can be made in the polypeptide chain for example, adding epitope tags, without impairing or eliminating its functions (Ausubel et al., Current Protocols in Molecular Biology, Greene Publ. Assoc. and Wiley-Intersciences, 1998). Other modifications that can be made without materially impairing one or more functions of a polypeptide include, for example, in vivo or in vitro chemical and biochemical modifications or the incorporation of unusual amino acids. In some examples, a functional fragment of a chemokine may consist of about 10 or more, about 25 or more, about 50 or more, about 75 or more, about 100 or more, about 125 or more, about 150, about 175 or more, or about more or 200 or more amino acid residues of a chemokine amino acid sequence.

In some examples, the chemokine or a functional fragment thereof has an amino acid that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, such as those detailed herein, for example using the NCBI Blast 2.0 gapped BLAST set to default parameters. Alignment may also be performed manually by inspection. One or more conservative amino acid modifications can also be made in the chemokine amino acid sequence, whether an addition, deletion or modification, that does not substantially alter the 3-dimensional structure of the polypeptide or its ability to bind to the cognate receptor. For example, a conservative amino acid substitution does not affect the ability of the chemokine to specifically bind its cognate receptor. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Peptides, such as chemokines and fragments thereof, can be modified by a variety of chemical techniques to produce derivatives having essentially the same activity or function-such as binding to a cognate receptor—as the unmodified peptides, and optionally having other desirable properties. For example, carboxylic acid groups of the protein, whether carboxyl-terminal or side chain, may be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C16 alkyl or dialkyl amino or further converted to an amide.

Hydroxyl groups of the peptide side chains can be converted to C1-C16 alkoxy or to a C1-C16 ester using well-recognized techniques. Phenyl and phenolic rings of the peptide side chains can be substituted with one or more halogen atoms, such as F, Cl, Br or I, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165 174 and Principles of Pharmacology Munson (ed.) 1995, Ch. 102, for descriptions of techniques used in CADD. Also included within the scope of the disclosure are mimetics prepared using such techniques.

Amino acids in a peptide, polypeptide, or protein generally are chemically bound together via amide linkages (CONH). Additionally, amino acids may be bound together by other chemical bonds. For example, linkages for amino acids or amino acid analogs can include CH2NH—, —CH2S—, —CH2-CH2-, —CH=CH— (cis and trans), —COCH2-, —CH(OH)CH2-, and —CHH2SO— (These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., Int J Pept Prot Res 14:177-185, 1979; Spatola et al. Life Sci 38:1243-1249, 1986; Harm J. Chem. Soc Perkin Trans. 1307-314, 1982; Almquist et al. J. Med. Chem. 23:1392-1398, 1980; Jennings-White et al. Tetrahedron Lett 23:2533, 1982; Holladay et al. Tetrahedron. Lett 24:4401-4404, 1983; and Hruby Life Sci 31:189-199, 1982.

Chemokines MIP1γ (CCL9), MRP-2 (CCL10), MIp-1δ (CCL15) and CCL23 appear to bind CCR1 only, Chemokines Eotaxin, Eotaxin-2 only bind CCR3, Chemokine MIP1β (CCL4) only binds CCR5, Chemokine MIP3a (CCL20) only binds to CCR6, More specifically, each of MCP-1, MCP-2, MCP-3, MCP-4, MCP-5, MIP-3alpha, MIG (CXCL9), IP10 (CXCL10), CXCL11 (I-TAC) and RANTES are useful for removing one or more of CCR2, CCR6, CCR3, CCR5, CCR1, CXCR3 and/or CCR9 expressing cells from the blood of a patient. In specific embodiments, the chemokine is selected from MCP-1, MCP-2, MCP-3, MCP-4 and MCP-5 and the chemokine receptor is CCR2. In other embodiments, the chemokine is MIP-3a and the chemokine receptor is CCR6. In still further embodiments, the chemokine is RANTES and the chemokine receptor is selected from CCR3, CCR1, CCR5 or CCR9.

The chemokines described in greater detail herein (with reference to the relevant figures and amino acid sequences, as set forth in the SEQ ID NOs and the corresponding experimental examples) may each be applied according to the present invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC1 1, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5 as available on 13 Jun. 2011, which is incorporated herein by reference in its entirety.

CCL20 is the gene symbol approved by the HUGO Gene Nomenclature Committee for chemokine (C—C motif) ligand 20, also known as MIP-3alpha. The HGNC ID for this gene is 10619. The gene is located at chromosome position 2q33-q37. The previous symbol and name for the gene is SCYA20, "small inducible cytokine subfamily A (Cys-Cys), member 20". Synonyms for this gene include CKb4, exodus-1, LARC, MIP-3a, ST38. The Genbank reference sequence for CCL20 is D86955.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)".

Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CXCL11 is the gene symbol approved by the HUGO Gene Nomenclature Committee for chemokine (C—X—C motif) ligand 11. The HGNC ID for this gene is 10638. The gene is located at chromosome position 4q21. The previous symbol and name for the gene is SCYB9B, SCYB11, "small inducible cytokine subfamily B (Cys-X-Cys), member 11". Synonyms for this gene include b-R1, H174, I-TAC, IP-9. The Genbank reference sequence for CXCL11 is U66096.1 as available on 13 Jun. 2011, which is incorporated herein by reference in its entirety.

CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECK-var", "thymus expressed chemokine". The Genbank reference sequence for CCL25 is U86358.1 as available on 13 Jun. 2011, which is incorporated herein by reference in its entirety.

CXCL10 is the gene symbol approved by the HUGO Gene Nomenclature Committee for chemokine (C—X—C motif) ligand 10. The HGNC ID for this gene is 10637. The gene is located at chromosome position 4q21. The previous symbol and name for the gene is INP10, SCYB10, "small inducible cytokine subfamily B (Cys-X-Cys), member 10". Synonyms for this gene include C7, crg-2, gIP-10, IFI10, IP-10, mob-1. The Genbank reference sequence for CXCL10 is X02530.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine (or any other amino acid such as ornithine and diaminopropionic acid, that may be biotinylated), as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 1. The amino acid sequence of the mature protein is set forth as SEQ ID NO: 2. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SED ID NO:3.

Accordingly, in certain embodiments the invention also provides a modified MCP-1 chemokine comprising, consisting essentially of or consisting of the amino acid sequence set forth as SEQ ID NO: 1, SEQ ID NO: 2 or SEQ ID NO: 3 in which one or more of the following modifications have been made:

a) the glutamine residue 1 of SEQ ID NO: 2 has been replaced with pyroglutamine b) the C terminus is produced as an amide derivative (this may be achieved by synthesis on an amide linker)

c) the (C terminal region) residue at position 98 of SEQ ID NO: 1 or position 75 of SEQ ID NO:2 or position 67 of SEQ ID NO: 3, which may be a lysine or ornithine residue, is biotinylated, optionally via a spacer group, in order to permit immobilization of the chemokine on a solid support; and/or d) the methionine residue at position 87 of SEQ ID NO: 1 or position 64 of SEQ ID NO: 2 or position 56 of SEQ ID NO: 3 has been replaced with norleucine.

The (C terminal region) amino acid, which may be a lysine residue or a functional equivalent, at position 98 of SEQ ID NO: 1 or position 75 of SEQ ID NO:2 or position 67 of SEQ ID NO: 3 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 7 to 9 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 4. The amino acid sequence of N-terminal processed MCP-5 chemokine is 82 amino acids long and is set forth as SEQ ID NO: 5. An amino acid sequence alignment suggests that MCP-5 has a C-terminal extension when compared to the amino acid sequence of MCP-1. The results of this alignment are shown in FIG. 10. C-terminal truncated versions of MCP-5 can thus be synthesised. This truncated version will comprise, consist essentially of or consist of MCP-5 residues 1-76, set forth as SEQ ID NO: 6.

Accordingly, in certain embodiments the invention also provides a modified MCP-5 chemokine comprising the amino acid sequence set forth as SEQ ID NO: 4, SEQ ID NO: 5 or SEQ ID NO: 6 in which the isoleucine residue at position 97 of SEQ ID NO: 4 or at position 75 of SEQ ID NO: 5 or SEQ ID NO: 6 has been replaced with lysine (or a functional equivalent such as ornithine or diaminopropionic acid, which can be biotinylated). In certain embodiments, the modified MCP-5 chemokine comprises, consists essentially of or consists of the amino acid sequence of SEQ ID NO: 7. The modified MCP-5 chemokine may be biotinylated at the lysine (or a functional equivalent) residue at position 97 of SEQ ID NO: 4 or at position 75 of SEQ ID NO: 5 or SEQ ID NO: 6. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 11. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

An example of a CCL25 chemokine of the various embodiments of the invention containing both modifications and a truncation and specifically adapted for use in the invention is described in WO2010/029317, incorporated herein by reference. Reference may also be made to Example 12 below and SEQ ID NOs 23 to 25.

A further example of a chemokine of the various embodiments of the invention containing modifications and specifically adapted for use in the invention is described in detail herein (see Example 8 below). The modified CCL2 (MCP-1) corresponds to residues 1 to 76 of the full length mature protein (and lacks the N-terminal signal peptide of 23 amino acids, which is cleaved off) and thus retains the chemokine fold. The Gln at the N-terminus of the protein (Gln1) is substituted with pyroglutamine to prevent mixed species of N-terminal Gln and pyroGlu being generated (SEQ ID NO: 8). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 9). A suitable spacer, such as a PEG spacer, may be incorporated between the ε-amino functionality and the biotin. Thus, the invention relates to a modified chemokine, including a biotinylated version, which comprises, consists essentially of or consists of the amino acid sequence of SEQ ID NO: 10:

H-XPDAINAPVTCCYNFTNRKISVQRLASYRRITSSKCPKEAVIFKTIVA

KEICADPKQKWVQDSMDHLDKQTQTPXT-NH$_2$

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Example 3 below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 11). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 12). The naturally occurring lysine at position 75 is modified through biotinylation. A suitable spacer, such as a PEG spacer, may be incorporated between the ε-amino functionality and the biotin (SEQ ID NO: 13):

Thus, in certain embodiments the invention also relates to a modified chemokine comprising, consisting essentially of or consisting of the amino acid sequence of SEQ ID NO: 13:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Example 9 below). The modified CCL11 (Eotaxin) corresponds to residues 1 to 74 of the full length mature protein (and lacks the N-terminal signal peptide of 23 amino acids, which is cleaved off) and thus retains the chemokine fold (SEQ ID NO: 14). The lysine at position 73 may be modified through biotinylation. FmocLys(ivDde)-OH is incorporated as residue 73 to facilitate site-specific labelling at this position of the protein (SEQ ID NO: 15). A suitable spacer, such as a PEG spacer, may be incorporated between the ε-amino functionality and the biotin. The biotinylated version comprises, consists essentially of or consists of the amino acid sequence of SEQ ID NO:16.

Thus, in other embodiments the invention also relates to a modified chemokine comprising, consisting essentially of or consisting of the amino acid sequence of SEQ ID NO: 14 or SEQ ID NO: 16:

```
                                         SEQ ID NO: 14
GPASVPTTCCFNLANRKIPLQRLESYRRITSGKCPQKAVIFKTKLAKDIC

ADPKKKWVQDSMKYLDQKSPTPXP
```

X is an amino acid residue that can be biotinylated, such as lysine, ornithine or diaminopropionic acid and optionally is biotinylated, optionally via a spacer molecule such as PEG, e.g. K(PEG-Biotin).

```
                                         SEQ ID NO: 16
H-GPASVPTTCCFNLANRKIPLQRLESYRRITSGKCPQKAVIFKTKLAKD

ICADPKKKWVQDSMKYLDQKSPTPXP-NH2
```

X is K(PEG-Biotin)

A further example of a chemokine of the various embodiments of the invention containing modifications and specifically adapted for use in the invention is described in detail herein (see Example 10 below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 17). This Met to Lys substitution provides a lysine at position 67 which can be modified through biotinylation. FmocLys (ivDde)-OH is incorporated as residue 67 to facilitate site-specific labelling at this position of the protein (SEQ ID NO: 18). The biotinylated version comprises, consists essentially of or consists of the amino acid sequence of SEQ ID NO: 19.

Thus, in other embodiments the invention also relates to a modified chemokine comprising, consisting essentially of or consisting of the amino acid sequence of SEQ ID NO: 19:

```
SPYSSDTTPCCFAYIARPLPRAHIKEYFYTSGKCSNPAVVFVTRKNRQVC

ANPEKKWVREYINSLEXS
```

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Example 11 below). The modified CCL20 (MIP-3a) corresponds to residues 1 to 70 of the full length mature protein (and lacks the N-terminal signal peptide of 26 amino acids, which is cleaved off) and thus retains the chemokine fold (SEQ ID NO: 20). FmocLys(ivDde)-OH is incorporated as residue 68 to facilitate site-specific labelling at this position of the protein (SEQ ID NO: 21). The naturally occurring lysine at position 68 is modified through biotinylation. A PEG spacer may be incorporated between the ε-amino functionality and the biotin. The final protein may thus comprise, consist essentially of or consist of the amino acid sequence of SEQ ID NO: 22.

Thus, in certain embodiments the invention also relates to a modified chemokine comprising, consisting essentially of or consisting of the amino acid sequence of SEQ ID NO: 22:

```
ASNFDCCLGYTDRILHPKFIVGFTRQLANEGCDINAIIFHTKKKLSVCAN

PKQTWVKYIVRLLSKKVXNM
```

X is an amino acid residue that can be biotinylated, such as lysine, ornithine or diaminopropionic acid and optionally is biotinylated, optionally via a spacer molecule such as PEG, in particular K(PEG-Biotin)

A further example of a chemokine of the various embodiments of the invention containing modifications and specifically adapted for use in the invention is described in detail herein (see Example 13 below). The modified CXCL11 (ITAC) corresponds to residues 1 to 73 of the full length mature protein (and lacks the N-terminal signal peptide of 21 amino acids, which is cleaved off) and thus retains the chemokine fold (SEQ ID NO: 26). An additional lysine is inserted at the C-terminus, optionally via a PEG spacer, at position 74. The chemokine may thus comprise, consist essentially of or consist of the amino acid sequence of SEQ ID NO: 28.

```
SEQ ID NO: 28:
FPMFKRGRCLCIGPGVKAVKVADIEKASIMYPSNNCDKIEVIITLKENKG

QRCLNPKSKQARLIIKKVERKNFX
```

X is an amino acid residue that can be biotinylated, such as lysine, ornithine or diaminopropionic acid and optionally is biotinylated, optionally via a spacer molecule such as PEG. The amino acid residue may be added via a spacer molecule such as PEG and may thus be "PEG-K".

FmocLys(ivDde)-OH is incorporated, following Fmoc-12-amino-4,7,10-trioxadodecanoic acid, as residue 74 to facilitate site-specific labelling at this position of the protein (SEQ ID NO: 27). The ε-amino side chain functionality of the additional Lys(74) is modified through biotinylation. The final protein may thus comprise, consist essentially of or consist of the amino acid sequence of SEQ ID NO: 28 where residue 74 is PEG-K.

A further example of a chemokine of the various embodiments of the invention containing modifications and specifically adapted for use in the invention is described in detail herein (see Example 14 below). The modified CXCL10 (IP-10) corresponds to residues 1 to 77 of the full length mature protein (and lacks the N-terminal signal peptide of 21 amino acids, which is cleaved off) and thus retains the chemokine fold. An amino acid which is capable of biotinylation, such as lysine or ornithine for example, may be inserted as residue 78. Insertion may be via a spacer, such as a PEG spacer. The linear amino acid sequence (SEQ ID NO: 29) is shown, prior to attachment of the PEG spacer, additional lysine and biotin molecules:

VPLSRTVRCTCISISNQPVNPRSLEKLEIIPASQFCPRVEIIATMKKKGE

KRCLNPESKAIKNLLKAVSKERSKRSP

Thus, position 78 may be modified through biotinylation. FmocLys(ivDde)-OH may be incorporated as residue 78 to facilitate site-specific labelling at this position of the protein (SEQ ID NO: 30). A suitable spacer, such as a PEG spacer, may be incorporated between the ε-amino functionality and the biotin. The biotinylated version comprises, consists essentially of or consists of the amino acid sequence of SEQ ID NO: 31.

Thus, in certain embodiments the invention also relates to a modified chemokine comprising, consisting essentially of or consisting of the amino acid sequence of SEQ ID NO: 31:

VPLSRTVRCTCISISNQPVNPRSLEKLEIIPASQFCPRVEIIATMKKKGE

KRCLNPESKAIKNLLKAVSKERSKRSPX

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

The specific chemokines, including derivatives thereof as described herein, newly synthesised for use in the methods of the invention may represent separate aspects of the invention. Biotinylation is positioned so as to permit immobilisation whilst retaining receptor binding capability.

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')$_2$ fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 1 below. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 1

Commercially available fluorophore labelled antibodies against specific chemokine receptors

| Antibody | Fluorophore | Supplier |
| --- | --- | --- |
| CCR5 | PE | Biolegend |
| CCR2 | PerCP Cy5.5 | Biolegend |
| CCR6 | PerCP Cy5.5 | BD Biosciences |
| CCR3 | PE | Biolegend |
| CCR1 | Alexa Fluor 647 | Biolegend |
| CCR9 | APC | R&D Systems |

Anti-CCR2 antibodies are described for example in WO 2010/021697, incorporated herein by reference. Further examples of potentially useful antibodies include MLN- 1202, an anti-CCR2 monoclonal antibody currently undergoing clinical trials (Millennium Pharmaceuticals).

The chemokine receptor expressing cells may thus be targeted using alternative binding agents, such as antibodies or other chemical compounds, as defined herein, rather than the natural chemokine binding partner. This approach is a new approach to treating inflammatory conditions and in particular multiple sclerosis.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition (in particular MS) comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focused therapeutic aspects of the various embodiments of the invention and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR2, CCR6, CCR3, CCR5, CCR1, CXCR3 and/or CCR9) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody—antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')$_2$ fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for conditions associated with multiple sclerosis. The column acts to specifically remove one or more of CCR2, CCR6, CCR3, CCR5, CCR1, CXCR3 and/or CCR9-expressing monocytes by exploiting the interaction between CCR2, CCR6, CCR3, CCR5, CCR1, CXCR3 and/or CCR9 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 3) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 4. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 5. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR2, CCR6, CCR3, CCR5, CCR1, CXCR3 and/or CCR9) chemokine receptor expressing cells to the patient. This is then a complete leukapheresis treatment method. Thus, a leukaphereis method, for treating multiple sclerosis, comprises collecting peripheral blood from the patient; applying the peripheral blood to an apheresis column loaded with a solid support comprising one or more binding reagents capable of specifically binding to one or more chemokine receptors, in particular the chemokine receptor CCR2, CCR6, CCR3, CCR5, CCR1, CXCR3 and/or CCR9, immobilized directly or indirectly on the support thus removing one or more of CCR2, CCR6, CCR3, CCR5, CCR1, CXCR3 and/or CCR9 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the (inflammatory) multiple sclerosis.

The methods of the various embodiments of the invention and binding reagents for use in the methods of the various embodiments of the invention may require that the patient has been selected for treatment on the basis of detecting an increase in the level of chemokine receptor, in particular, one or more of CCR2, CCR6, CCR3, CCR5, CCR1, CXCR3 and/or CCR9 expressing cells in a sample obtained from the patient. Such companion diagnostic methods are described in greater detail herein and are based, for example, on the observation that CCR2, CCR6, CCR3, CCR5, CCR1, CXCR3 and/or CCR9 expression may be elevated in patients with multiple sclerosis. More specifically, it is shown herein that levels of CCR2 and CCR6 expressing leukocytes, in particular T lymphocytes, are increased in MS patients (compared with healthy controls).

Thus, (in this context) in certain embodiments the invention also provides a method of diagnosing, monitoring progression of, or monitoring treatment of multiple sclerosis comprising determining:

a) the levels of one or more of the chemokine receptor CCR2, CCR6, CCR3, CCR5, CCR1, CXCR3 and/or CCR9 expressing cells b) levels of expression of one or more of CCR2, CCR6, CCR3, CCR5, CCR1, CXCR3 and/or CCR9; and/or c) levels of cells with high expression of one or more of CCR2, CCR6, CCR3, CCR5, CCR1, CXCR3 and/or CCR9 in a sample obtained from a subject, wherein high levels of one or more of CCR2, CCR6, CCR3, CCR5, CCR1, CXCR3 and/or CCR9 expressing cells, high levels of expression of one or more of CCR2, CCR6, CCR3, CCR5, CCR1, CXCR3 and/or CCR9 or high levels of cells with high expression of one or more of CCR2, CCR6, CCR3, CCR5, CCR1, CXCR3 and/or CCR9 or increased levels of one or more of CCR2, CCR6, CCR3, CCR5, CCR1, CXCR3 and/or CCR9 expressing cells compared to control, increased levels of expression of one or more of CCR2, CCR6, CCR3, CCR5, CCR1, CXCR3 and/or CCR9 compared to a control or increased levels of cells with high expression of one or more of CCR2, CCR6, CCR3, CCR5, CCR1, CXCR3 and/or CCR9 compared to a control indicate the presence or progression of multiple sclerosis. Levels of chemokine receptor expression, as opposed to cell numbers, may also be investigated as increased levels of chemokine receptor expression per cell may also be diagnostically relevant. The cells may be lymphoctes, in particular T cells.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to multiple sclerosis by identifying levels of one or more of CCR2, CCR6, CCR3, CCR5, CCR1, CXCR3 and/or CCR9 expression linked to conditions associated with an multiple sclerosis. Thus patients at risk may be identified before the disease has a chance to manifest itself in terms of symptoms identifiable in the patient. In certain embodiments, diagnosis may be made in conjunction with other objective indicators of multiple sclerosis. Thus, in specific embodiments, diagnosis is made in conjunction with one or more of the following indicators: clinical measures, multiple sclerosis severity score, MRI and ologoclonal immunoglobulin pattern in a suitable sample such as liquor.

"Monitoring progression of" includes performing the methods to monitor the stage and/or the state and progression of the multiple sclerosis. Monitoring progression may involve performing the diagnostic methods multiple times on the same patient to determine whether the levels of one or more of CCR2, CCR6, CCR3, CCR5, CCR1, CXCR3 and/or CCR9 expressing cells are increasing, decreasing or remaining stable over a certain time period. This may be in the context of a treatment regime.

"Monitoring the success of a particular treatment" is defined to include determining the levels of one or more of CCR2, CCR6, CCR3, CCR5, CCR1, CXCR3 and/or CCR9 expressing cells before and after a treatment. The treatment is generally one aimed at treating multiple sclerosis and may be a treatment according to one of the methods of the various embodiments of the invention as defined herein. Successful treatment may be determined with reference to a decrease in one or more of CCR2, CCR6, CCR3, CCR5, CCR1, CXCR3 and/or CCR9 expressing cells as a result of, or following, the treatment. Thus, in such methods a level of one or more of CCR2, CCR6, CCR3, CCR5, CCR1, CXCR3 and/or CCR9 expressing cells is determined prior to treatment. This level is recorded and a further assessment made at a predetermined time following the treatment. The comparison of levels of one or more of CCR2, CCR6, CCR3, CCR5, CCR1, CXCR3 and/or CCR9 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR2, CCR6, CCR3, CCR5, CCR1, CXCR3 and/or CCR9, expressing cells from the peripheral blood of the patient. In specific embodiments, at least around 50% depletion is achieved in a single treatment. Thus, successful treatment may be defined with reference to depletion of one or more of CCR2, CCR6, CCR3, CCR5, CCR1, CXCR3 and/or CCR9 expressing cells. Treatment may lead to depletion of between approximately 100 and 500 million one or more of CCR2, CCR6, CCR3, CCR5, CCR1, CXCR3 and/or CCR9 expressing cells, such as monocytes or lymphocytes, in particular T-cells, in certain embodiments. Additional factors may be included to determine successful treatment. For example, a lack of increase in one or more of CCR2, CCR6, CCR3, CCR5, CCR1, CXCR3 and/or CCR9 expressing cells following treatment may indicate successful treatment in terms of preventing further progression of the condition, optionally combined with an improvement in other markers or staging of the multiple sclerosis.

In specific embodiments, the multiple sclerosis is selected from active and stable relapsing-remitting multiple sclerosis.

The sample in which one or more of CCR2, CCR6, CCR3, CCR5, CCR1, CXCR3 and/or CCR9 expressing cell levels, levels of expression of one or more of CCR2, CCR6, CCR3, CCR5, CCR1, CXCR3 and/or CCR9 and/or levels of cells with high expression of one or more of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$, $CCR6^{hi}$, $CCR3^{hi}$, $CCR5^{hi}$, $CCR1^{hi}$ or $CCR9^{hi}$) are determined may comprise any suitable tissue sample or body fluid sample. Generally, the test sample is obtained from a human subject. Typically, the sample is a blood sample, in particular a peripheral blood sample. The sample may comprise cerebrospinal fluid (liquor) in certain embodiments. The methods may involve determining levels of one or more of CCR2, CCR6, CCR3, CCR5, CCR1, CXCR3 and/or CCR9 expressing monocytes, macrophages or lymphocytes in certain embodiments, such as CCR2 and/or CCR6 expressing T-cells.

Levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) may be determined according to any suitable method. For example, flow cytometry may be employed in order to determine the number of cells expressing CCR2, CCR6, CCR3, CCR5, CCR1, CXCR3 and/or CCR9 in the sample, to determine levels of CCR2, CCR6, CCR3, CCR5, CCR1, CXCR3 and/or CCR9 expression and/or to identify levels of $CCR2^{hi}$, $CCR6^{hi}$, $CCR3^{hi}$, $CCR5^{hi}$, $CCR1^{hi}$, $CXCR3^{hi}$ and/or $CCR9^{hi}$ cells. Flow cytometric techniques are described herein and examples of commercially available antibodies suitably labelled for use in flow cytometry are set out in Table 1 for example. Alternatively, the method may involve steps of collecting and fixing the cells in the sample, followed by incubation with a suitable binding reagent that binds specifically to the CCR2, CCR6, CCR3, CCR5, CCR1, CXCR3 and/or CCR9 chemokine receptor expressing cells in the sample. Any suitable binding reagent, as defined herein, may be employed. For example, a CCR2, CCR6, CCR3, CCR5, CCR1, CXCR3 and/or CCR9 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR2, CCR6, CCR3, CCR5, CCR1, CXCR3 and/or CCR9 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2) receptor expressing cell levels, to quantify levels of CCR2, CCR6, CCR3, CCR5, CCR1, CXCR3 and/or CCR9 expression and/or to quantify levels of $CCR2^{hi}$, $CCR6^{hi}$, $CCR3^{hi}$, $CCR5^{hi}$, $CCR1^{hi}$, $CXCR3^{hi}$ and/or $CCR9^{hi}$ cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR2, CCR6, CCR3, CCR5, CCR1, CXCR3 and/or CCR9 expressing cells to the solid support being determined following peripheral blood being passed through the column.

The levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) may be determined relative to a suitable control. When diagnosing multiple sclerosis, a threshold level of cells, level of expression of CCR2, CCR6, CCR3, CCR5, CCR1, CXCR3 and/or CCR9 and/or level of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) may be set at or over which a positive diagnosis is made. This threshold may be determined based upon measuring levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) in samples obtained from diseased patients and comparing these levels with levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) in samples obtained from healthy subjects.

In certain embodiments, multiple sclerosis is diagnosed on the basis of levels of chemokine receptor expressing cells, such as CCR2, CCR6, CCR3, CCR5, CCR1, CXCR3 and/or CCR9 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, multiple sclerosis is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, multiple sclerosis is diagnosed on the basis of levels of CCR2 or CCR6 expressing cells, such as lymphocytes and in particular T lymphocytes. A positive diagnosis may be made in subjects based upon the presence of greater than about 7%, greater than about 10% or greater than about 15% CCR2 expressing T cells in the sample, as a percentage of total cells in the sample. A positive diagnosis may be made in subjects based upon the presence of greater than about 18%, greater than about 20% or greater than about 22% CCR6 expressing T cells in the sample, as a percentage of total cells in the sample. Multiple sclerosis may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in CCR2 or CCR6 expressing cells, such as lymphocytes and in particular T lymphocytes, relative to healthy controls.

In certain embodiments, progression of multiple sclerosis, which may be in the context of a treatment regime, is monitored on the basis of levels of chemokine receptor expressing cells at different time points. Progression of multiple sclerosis may be indicated in subjects based upon an increase of greater than about 3%, greater than about 4%, greater than about 5%, such as an increase of greater than about 6%, greater than about 7%, greater than about 8%, greater than about 9%, greater than about 10%, greater than about 12%, greater than about 15%, greater than about 20%, greater than about 25%, greater than about 30%, greater than about 35%, greater than about 40%, greater than about 45% or more chemokine receptor expressing cells in the sample, as a percentage of total cells in the sample, compared to a sample taken from the same subject at an earlier time point. In other embodiments, progression of multiple sclerosis is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, multiple sclerosis is monitored on the basis of levels of CCR2 or CCR6 expressing cells, such as lymphocytes and in particular T lymphocytes. Progression of the disease, which may be in the context of a treatment regime, may be indicated in subjects based upon the presence of an increase of greater than about 3%, greater than about 4%, greater than about 5%, such as an increase of greater than about 6%, greater than about 7%, greater than about 8%, greater than about 9%, greater than about 10%, greater than about 12%, greater than about 15%, greater than about 20%, greater than about 25%, greater than about 30%, greater than about 35%, greater than about 40%, greater than about 45% or more chemokine receptor expressing cells in the sample, as a percentage of total cells in the sample, compared to a sample taken from the same subject at an earlier time point. In other embodiments, progression of multiple sclerosis is confirmed on the basis of the presence of a about a 1.2 fold or greater increase, such as about a 1.5, 2, 2.5, 3, 3.5, 4, 4.5, 5, 10, 20, 50 or 100 or greater fold increase in CCR2 or CCR6 expressing cells, such as lymphocytes and in particular T lymphocytes, relative to a sample taken from the same subject at an earlier time point.

Regression or successful treatment may be monitored based upon similar decreases over various time points. For example, regression or successful treatment may be indicated in subjects based upon a decrease of about 3%, such as a decrease of about 4%, about 5%, about 6%, about 7%, about 8%, about 9%, about 10%, about 12%, about 15%, about 20%, about 25%, about 30%, about 35% or more chemokine receptor expressing cells in the sample, as a percentage of total cells in the sample, compared to a sample taken from the same subject at an earlier time point. In other embodiments, regression of multiple sclerosis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, multiple sclerosis is monitored on the basis of levels of CCR2 or CCR6 expressing cells, such as lymphocytes and in particular T lymphocytes. Regression or successful treatment of the disease may be made in subjects based upon a decrease of about 3%, such as a decrease of about 4%, about 5%, about 6%, about 7%, about 8%, about 9%, about 10%, about 12%, about 15%, about 20%, about 25%, about 30%, about 35% or more CCR2 or CCR6 expressing cells, such as lymphocytes and in particular T lymphocytes in the sample, as a percentage of total cells in the sample or by a decrease of about 3%, such as a decrease of about 4%, about 5%, about 6%, about 7%, about 8%, about 9%, about 10%, about 12%, about 15%, about 20%, about 25%, about 30%, about 35% or more CCR2 or CCR6 expressing cells, such as lymphocytes and in particular T lymphocytes chemokine receptor expressing cells in the sample, as a percentage of total cells in the sample, compared to a sample taken from the same subject at an earlier time point. In other embodiments, regression of multiple sclerosis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CCR2 or CCR6 expressing cells, such as lymphocytes and in particular T lymphocytes, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) can then be compared with that of the control sample to make the diagnosis. A control sample from a disease patient may also be tested in certain embodiments. Reference to controls permits relative levels ("high", "low" etc.) of CCR2, CCR6, CCR3, CCR5, CCR1, CXCR3 and/or CCR9 expressing cells in the test sample to be readily identified and the significance thereof interpreted. Reference to controls also permits relative levels of CCR2, CCR6, CCR3, CCR5, CCR1, CXCR3 and/or CCR9 expression ("high", "low" etc.) within the cell population to be determined and the significance thereof interpreted. Such determination may, for example, indicate the average levels of CCR2, CCR6, CCR3, CCR5, CCR1, CXCR3 and/or CCR9 expression per cell in the test sample.

Thus, in specific embodiments, high or higher levels of one or more of CCR2, CCR6, CCR3, CCR5, CCR1, CXCR3 and/or CCR9 expressing cells or high or higher levels of CCR2, CCR6, CCR3, CCR5, CCR1, CXCR3 and/or CCR9 expression, for example average CCR2, CCR6, CCR3, CCR5, CCR1, CXCR3 and/or CCR9 expression per cell, or high or higher levels of one or more of $CCR2^{hi}$, $CCR6^{hi}$, $CCR3^{hi}$, $CCR5^{hi}$, $CCR1^{hi}$, $CXCR3^{hi}$ and/or $CCR9^{hi}$ cells correlate with active disease or more active multiple sclerosis. Similarly, lower or low levels of one or more of CCR2, CCR6, CCR3, CCR5, CCR1 and CCR9 expressing cells, or low or lower levels of CCR2, CCR6, CCR3, CCR5, CCR1, CXCR3 and/or CCR9 expression, for example average CCR2, CCR6, CCR3, CCR5, CCR1, CXCR3 and/or CCR9 expression per cell, or low or lower levels of one or more of $CCR2^{hi}$, $CCR6^{hi}$, $CCR3^{hi}$, $CCR5^{hi}$, $CCR1^{hi}$ and $CCR9^{hi}$ cells may correlate with a lack of active inflammation or multiple sclerosis. This may be defined as "less active disease". It can readily be envisaged that control samples may be assessed and levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) determined across the range of severities of conditions associated with multiple sclerosis. This may assist in correlating the levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) in the test sample with the relative severity of the condition.

When monitoring progression of, or monitoring treatment of multiple sclerosis, the control samples may be taken from the subject at an earlier time point. They may, however, be based upon known reference values as discussed above. Thus, relative levels of CCR2, CCR6, CCR3, CCR5, CCR1, CXCR3 and/or CCR9 expressing cells, relative levels of CCR2, CCR6, CCR3, CCR5, CCR1, CXCR3 and/or CCR9 expression including relative levels of average CCR2, CCR6, CCR3, CCR5, CCR1, CXCR3 and/or CCR9 expression per cell or relative levels of $CCR2^{hi}$, $CCR6^{hi}$, $CCR3^{hi}$, $CCR5^{hi}$, $CCR1^{hi}$, $CXCR3^{hi}$ and/or $CCR9^{hi}$ cells may be with reference to samples taken from the same subject at a different point in time. In certain embodiments, decreased levels of one or more of CCR2, CCR6, CCR3, CCR5, CCR1, CXCR3 and/or CCR9 expressing cells decreased relative levels of one or more of CCR2, CCR6, CCR3, CCR5, CCR1, CXCR3 and/or CCR9 expression including decreased relative levels of average CCR2, CCR6, CCR3, CCR5, CCR1, CXCR3 and/or CCR9 expression per cell, or decreased relative levels of one or more of $CCR2^{hi}$, $CCR6^{hi}$, $CCR3^{hi}$ $CCR5^{hi}$, $CCR1^{hi}$, $CXCR3^{hi}$ and/or $CCR9^{hi}$ cells correlate with successful treatment. The treatment may be any suitable treatment, but in specific embodiments is a treatment according to the various embodiments of the invention.

When monitoring progression of multiple sclerosis, increased levels of one or more of CCR2, CCR6, CCR3, CCR5, CCR1, CXCR3 and/or CCR9 expressing cells increased relative levels of one or more of CCR2, CCR6, CCR3, CCR5, CCR1, CXCR3 and/or CCR9 expression including increased relative levels of average CCR2, CCR6, CCR3, CCR5, CCR1, CXCR3 and/or CCR9 expression per cell or increased relative levels of one or more of $CCR2^{hi}$, $CCR6^{hi}$, $CCR3^{hi}$, $CCR5^{hi}$, $CCR1^{hi}$ and $CCR9^{hi}$ cells may indicate the progression of condition or disease. Thus, if levels of one or more of CCR2, CCR6, CCR3, CCR5, CCR1, CXCR3 and/or CCR9 expressing cells, levels of expression of one or more of CCR2, CCR6, CCR3, CCR5, CCR1, CXCR3 and/or CCR9 and/or levels of cells with high expression of one or more of CCR2, CCR6, CCR3, CCR5, CCR1, CXCR3 and/or CCR9 (defined as $CCR2^{hi}$, $CCR6^{hi}$, $CCR3^{hi}$, $CCR5^{hi}$, $CCR1^{hi}$, $CXCR3^{hi}$ and/or $CCR9^{hi}$) are increased in a sample taken later than a sample from the same patient this may indicate progression of the condition.

Since the levels of one or more of CCR2, CCR6, CCR3, CCR5, CCR1, CXCR3 and/or CCR9 expressing cells, levels of one or more of CCR2, CCR6, CCR3, CCR5, CCR1, CXCR3 and/or CCR9 expression or levels of one or more of $CCR2^{hi}$, $CCR6^{hi}$, $CCR3^{hi}$, $CCR5^{hi}$, $CCR1^{hi}$, $CXCR3^{hi}$ and/or $CCR9^{hi}$ cells are diagnostically relevant, determining such levels in a sample obtained from a subject may influence treatment selection for that subject. Accordingly, in certain embodiments the invention provides a method of selecting a suitable treatment for multiple sclerosis comprising determining:

a) the levels of the one or more of chemokine receptor CCR2, CCR6, CCR3, CCR5, CCR1, CXCR3 and/or CCR9 expressing cells b) levels of expression of one or more of CCR2, CCR6, CCR3, CCR5, CCR1, CXCR3 and/or CCR9; and/or c) levels of cells with high expression of one or more of CCR2, CCR6, CCR3, CCR5, CCR1, CXCR3 and/or CCR9 in a sample obtained from a subject, wherein high levels of one or more of CCR2, CCR6, CCR3, CCR5, CCR1, CXCR3 and/or CCR9 expressing cells, high levels of expression of one or more of CCR2, CCR6, CCR3, CCR5, CCR1, CXCR3 and/or CCR9 or high levels of cells with high expression of CCR2, CCR6, CCR3, CCR5, CCR1, CXCR3 and/or CCR9 or increased levels of one or more of CCR2, CCR6, CCR3, CCR5, CCR1, CXCR3 and/or CCR9 expressing cells compared to control, increased levels of expression of one or more of CCR2, CCR6, CCR3, CCR5, CCR1, CXCR3 and/or CCR9 compared to a control or increased levels of cells with high expression of one or more of CCR2, CCR6, CCR3, CCR5, CCR1, CXCR3 and/or CCR9 compared to a control, result in selection of a treatment as defined herein for treatment of the multiple sclerosis. In certain embodiments, the chemokine receptor expressing cells are high chemokine receptor expressing cells, in particular, high CCR2, CCR6, CCR3, CCR5, CCR1, CXCR3 and/or CCR9 expressing cells. The cells may be lymphocytes, in particular T-lymphocytes. The cells may be CCR2 and/or CCR6 expressing cells, such as T-cells, in specific embodiments.

In specific embodiments, multiple sclerosis is treated on the basis of measuring levels of chemokine receptor expressing cells, such as CCR2, CCR6, CCR3, CCR5, CCR1, CXCR3 and/or CCR9 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, multiple sclerosis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, multiple sclerosis is treated on the basis of measuring levels of CCR2 or CCR6 expressing cells, such as lymphocytes and in particular T lymphocytes. Thus, a treatment according to the various embodiments of the invention may be applied based upon the presence of greater than about 7%, greater than about 10% or greater than about 15% CCR2 expressing T cells in the sample, as a percentage of total cells in the sample. Thus, a treatment according to the various embodiments of the invention may be applied based upon the presence of greater than about 18%, greater than about 20% or greater than about 22% CCR6 expressing T cells in the sample, as a percentage of total cells in the sample. Alternatively, multiple sclerosis is treated on the basis of the presence of a about a 1.5 fold or greater increase, such as about a 2, 2.5, 3, 3.5, 4, 4.5, 5, 10, 20, 50 or 100 or greater fold increase in CCR2 or CCR6 expressing cells, such as lymphocytes and in particular T lymphocytes, relative to healthy controls.

For the avoidance of doubt, all embodiments described in respect of the methods of the various embodiments of the invention apply to these aspects mutatis mutandis and are not repeated for reasons of conciseness. Specifically, multiple sclerosis may be indicated in conjunction with one or more of the following indicators:
clinical measures, multiple sclerosis severity score, MRI and ologoclonal immunoglobulin pattern in a suitable sample such as liquor.

The multiple sclerosis may be selected from active and stable relapsing-remitting multiple sclerosis. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR2, CCR6, CCR3, CCR5, CCR1, CXCR3 and/or CCR9 expressing cells, such as monocytes, lymphocytes, neutrophils, macrophages, eosinophils and basophils (in particular T-cells, including CCR2 and/or CCR6 expressing T-lymphocytes), upregulated in multiple sclerosis, an important factor in the inflammatory process of multiple sclerosis can be controlled. The method of the invention may be effective in treating or reversing conditions such as active and stable relapsing-remitting multiple sclerosis.

The various embodiments of the invention will now be described in more detail by reference to the following non-limiting embodiments and examples:

DESCRIPTION OF PREFERRED EMBODIMENTS

In secondary progressive MS microglia/MØ present at border of plaques produce chemokines MCP-1 and CXCL10 responsible for attracting CCR2 and CXCR3 expressing cells including macrophages and astrocytes.

It is shown herein that subjects suffering from MS exhibit increased frequency of chemokine receptor expressing cells in the peripheral blood, in particular CCR2 and CCR6 expressing T lymphocytes, compared to healthy controls. It is also shown herein that the CCR2 cells can be removed using a suitable binding reagent, in particular MCP-1 (in biotinylated form) immobilized on a suitable matrix. Similarly, it is shown herein that (the additional) CCR6-expressing cells can be depleted using a suitable binding reagent, in particular CCL20 (MIP-31), in biotinylated form, immobilized on a suitable matrix.

The CCL5 levels are significantly elevated in cerebrospinal fluid of MS patients with relapsing disease demonstrating that circulating CCL5 is involved in recruiting CCL5 binding cells to the brain. These findings are supported by the enrichment of T cells in cerebrospinal fluid expressing CCR5 and CCR6 suggesting an active accumalation due to a chemokine gradient of CCL5. Therefore eliminating cells normally attracted to the brain by providing an extracorpeal source of CCL5 attached to a column will be useful for the treatment of MS.

Examples 1 and 2

Materials and Methods
Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled MCP-1 (in concentrations 10 ng/μL and 50 ng/μL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 1—Binding of Monocytes to MCP-1

Figure 1A:
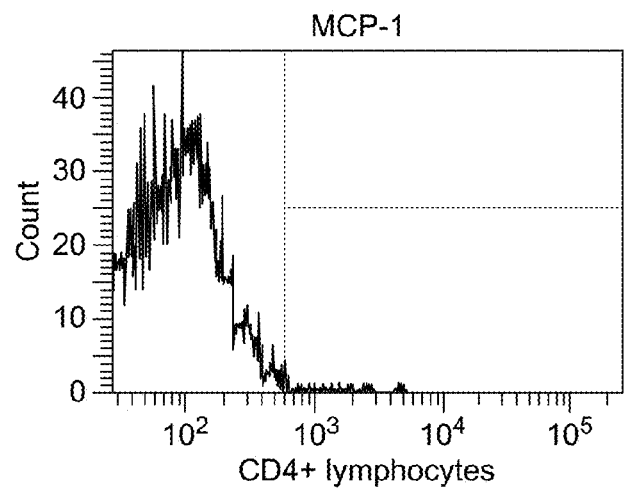
FIGS. 1a, 1b & 1c—the binding of biotinylized MCP-1 by CD4+, CD8+ T-cells and CD14+ monocytes respectively, obtained from peripheral blood of a healthy donor.
Figure 1B:
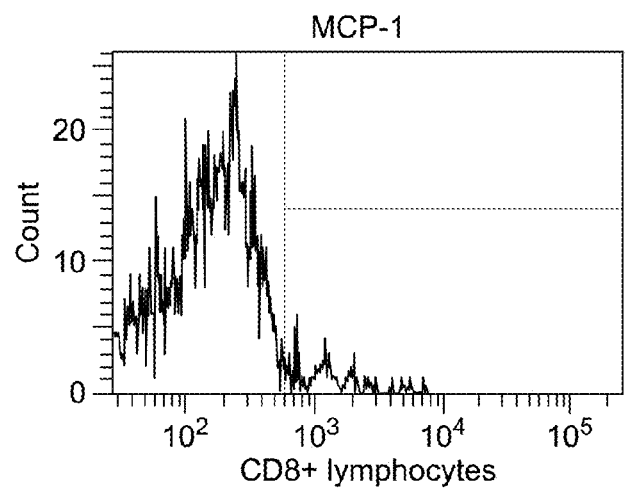
Figure 1C:
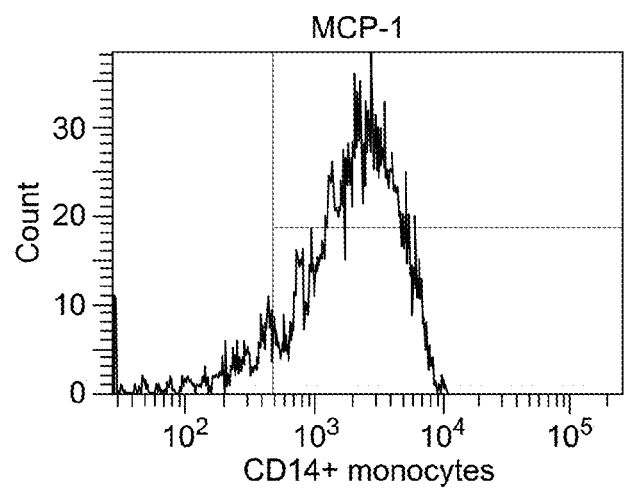

In the experiment with biotinylated MCP-1 it was found that about 90% of the monocytes obtained from peripheral blood of healthy donors had bound to the cytokine after 30 min of incubation (FIG. 1a), whereas CD4+ and CD8+ lymphocytes had not bound (FIGS. 1b and 1c).

Example 2

Figure 2A:
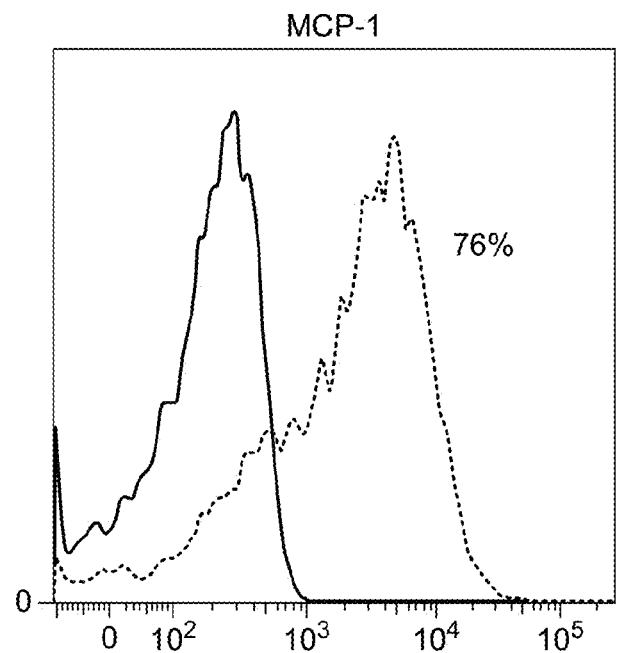
FIG. 2a—binding of MCP-1 to monocytes (dashed line) in peripheral blood taken from IBD patients. The graph represents a summary of four tests.
Figure 2B:
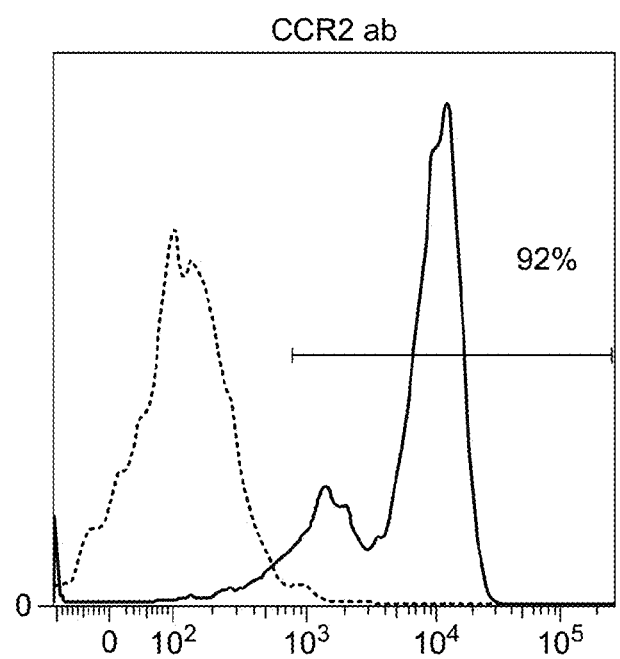
FIG. 2b—binding of CCR2-antibody to monocytes (line) in peripheral blood taken from IBD patients. The graph represents a summary of four tests.

Monocytes were investigated for their expression of CCR2 (FIG. 2b) and their ability to bind MCP-1 (FIG. 2a). CCR2 expression was noted an all monocytes with the majority of monocytes expressing high levels, using an anti-CCR2 antibody (FIG. 2b). The MCP-1 binding to monocytes shown in FIG. 2a corresponds to the CCR2hi expressing population shown in FIG. 2b. Thus, MCP-1 binds favourably to CCR2hi expressing cells.

Example 3—Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for multiple sclerosis. It will specifically remove CCR2, CCR6, CCR3, CCR5, CCR1, CXCR3 and/or CCR9-expressing leukocytes, in particular monocytes, through the use of a binding reagent, more specifically an MCP-1, MCP-2, MCP-3, MCP-4, MCP-5, MIP-3alpha, MIG (CXCL9), IP10 (CXCL10), CXCL11 (I-TAC), CCL25 and RANTES containing resin, exploiting the CCR2, CCR6, CCR3, CCR5, CCR1, CXCR3 and/or CCR9-chemokine interaction. The column consists of three combined components, the plastic house, the streptavidin (SA) Sepharose™ BigBeads matrix and one or more of biotinylated MCP-1, MCP-2, MCP-3, MCP-4, MCP-5, MIP-3alpha, MIG (CXCL9), IP10 (CXCL10), CXCL11 (I-TAC), CCL25 and RANTES bound to the matrix. The treatment is conducted using the same techniques as a standard apheresis procedure.

Figure 3:
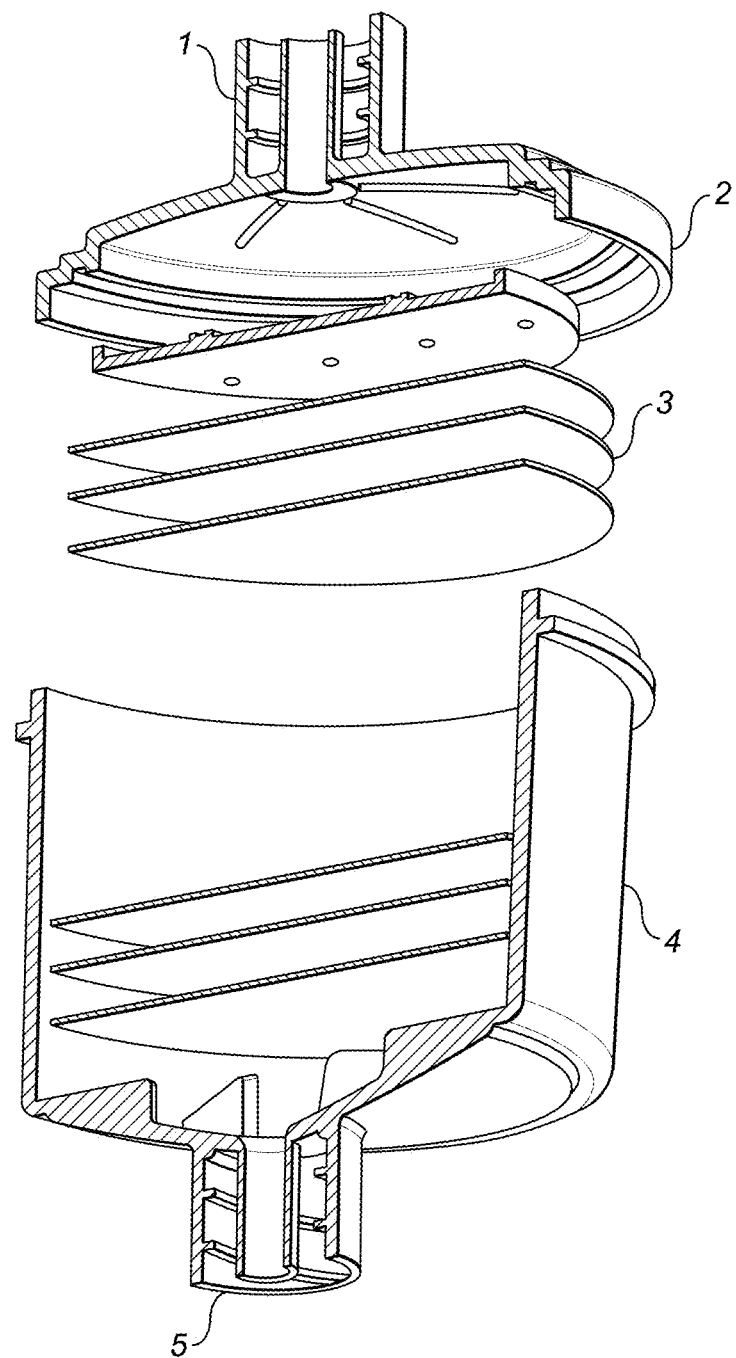
FIG. 3—The plastic house and top showing the distribution plate (2) and safety filter units (3 and 4).

The Plastic House (FIG. 3)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 3. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, the one or more binding reagents that bind specifically to CCR2, CCR6, CCR3, CCR5, CCR1, CXCR3 and/or CCR9. One or more chemokines such as those selected from the group consisting of MCP-1, MCP-2, MCP-3, MCP-4, MCP-5, MIP-3alpha, MIG (CXCL9), IP10 (CXCL10), CXCL11 (I-TAC), CCL25 and RANTES may be employed. These peptides may be synthetic, engineered versions of the human chemokine, which are truncated and biotinylated, but retain binding activity to the CCR2, CCR6, CCR3, CCR5, CCR1, CXCR3 and/or CCR9 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

Figure 4:
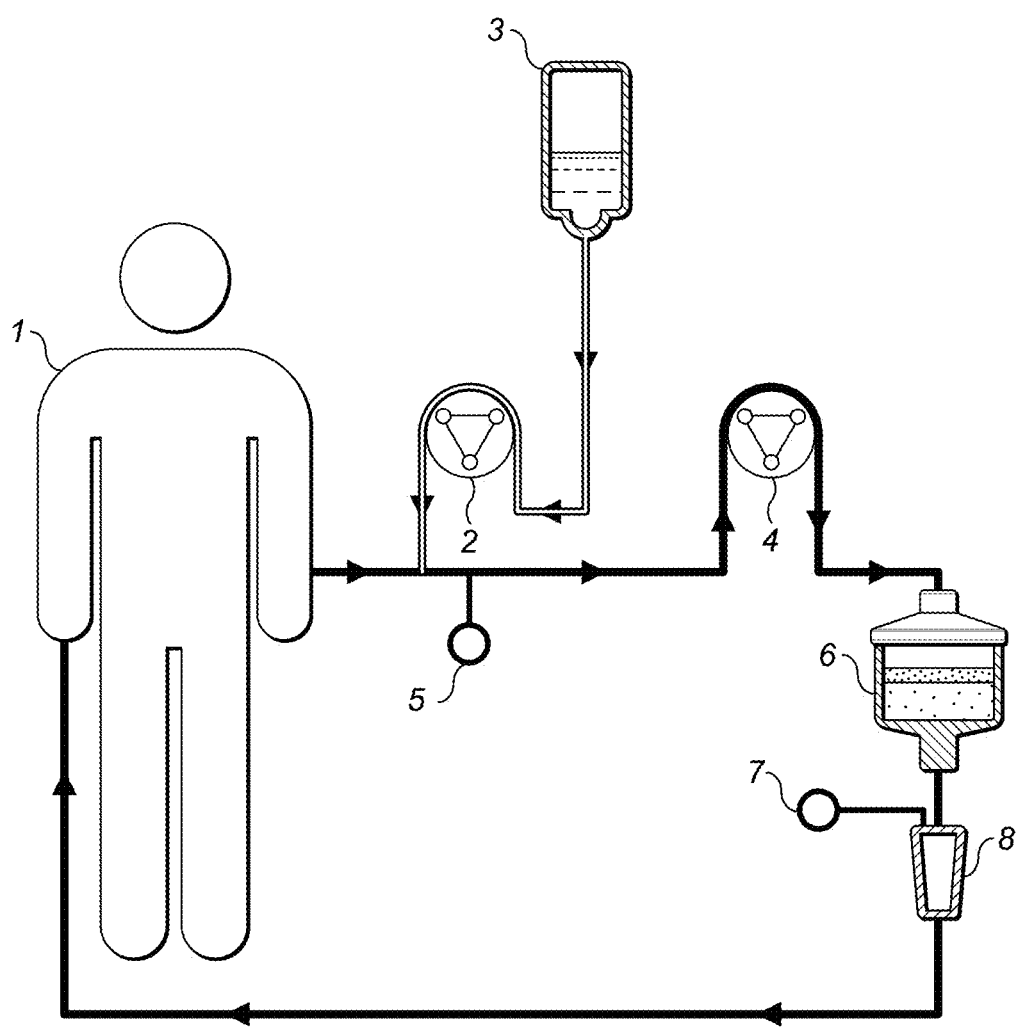
FIG. 4—The overall leukapheresis system

The system is illustrated in FIG. 4. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

Figure 5:
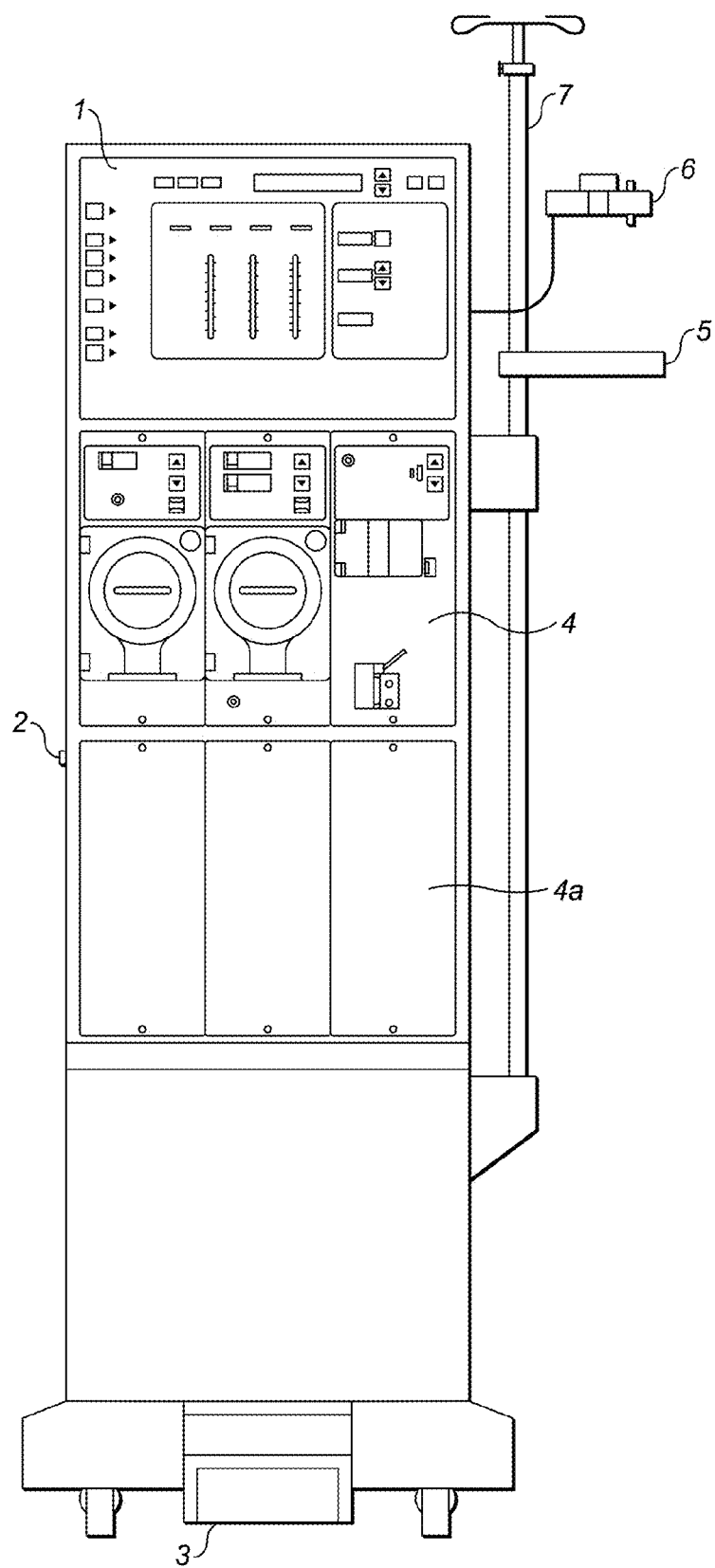
FIG. 5—The pump with air detector and optical detector (4).

A schematic diagram of the pump, showing the air detector and optical filter is shown in FIG. 5. If the pump system detects air bubbles and optical fluctuations or if extracorporeal pressure values are out of the set range, then the pump stops immediately and a visual/audible alarm are emitted.

LEGEND FOR FIG. 5

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations—MCP-1

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

Figure 6A:
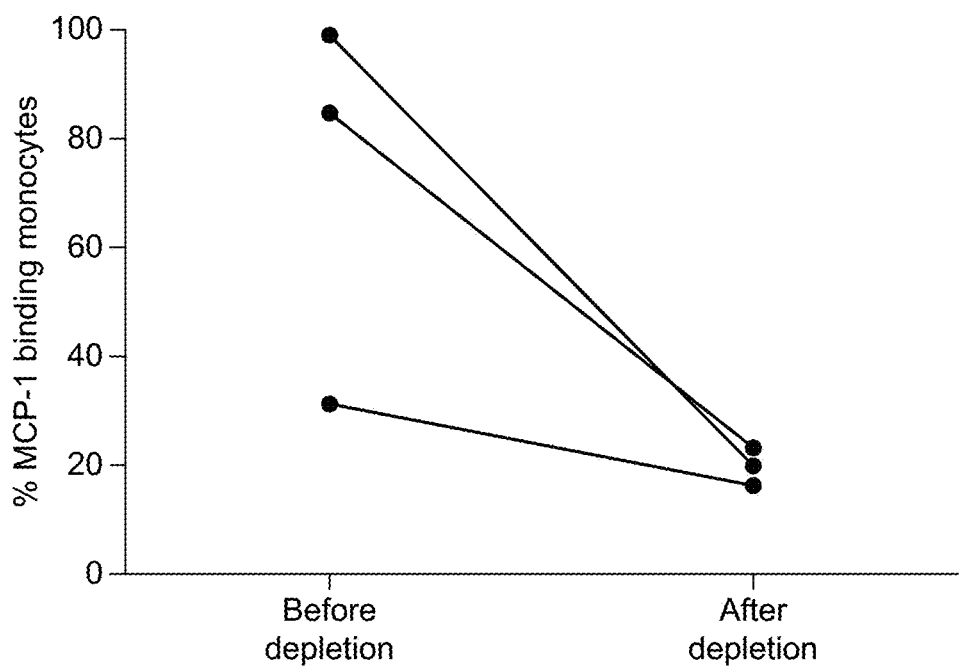
FIG. 6a—Results of in vitro depletion tests performed on the bMCP-1 coupled matrix showing ability to eliminate CCR2-expressing cells from blood from three healthy donors.

The results demonstrate significant depletion of the target population CCR2-expressing monocytes post matrix perfusion. Depletion tests were performed on blood from three healthy donors. The results are shown in FIG. 6a.

In conclusion, the in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

In-Vitro Depletion of Target Cell Populations—RANTES

To investigate the ability to eliminate CCR1, 3 and 5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR1, 3 and 5-expressing cells.

Figure 6B:
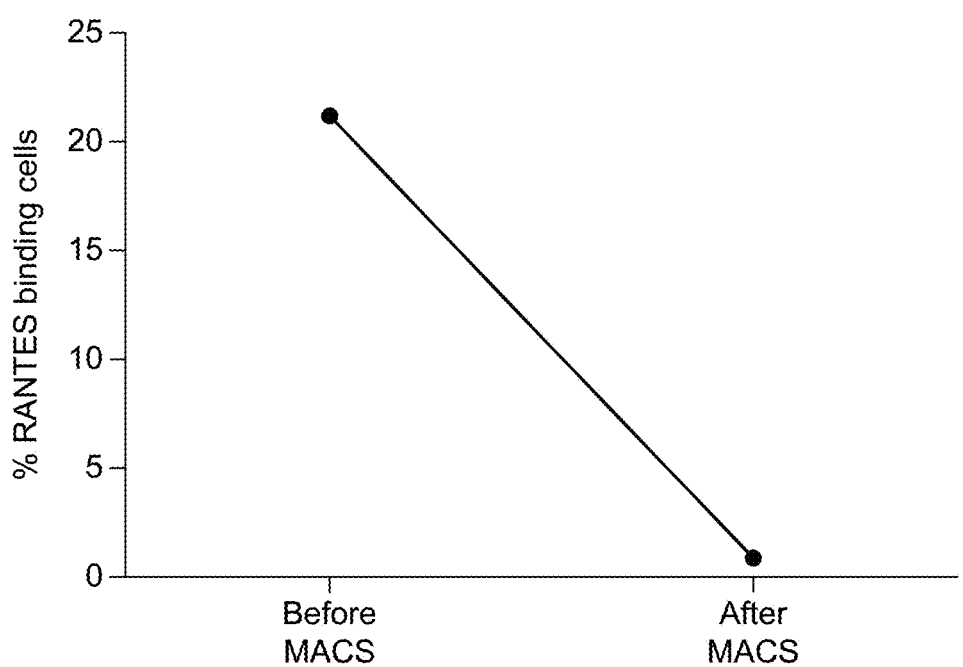
FIG. 6b—Results of in vitro depletion tests performed on the biotinylated RANTES coupled matrix showing ability to eliminate chemokine receptor-expressing cells from peripheral blood of a healthy donor.

The results demonstrate significant depletion of the target population chemokine receptor-expressing cells post matrix perfusion. Depletion tests were performed on blood from a healthy donor. The results are shown in FIG. 6b.

The in-vitro results demonstrate a specific reduction of around 20% of the chemokine receptor-expressing cells by the column. Non-CCR1, 3 or 5-expressing cells remained unaffected (data not shown).

In-Vitro Depletion of Target Cell Populations—MIP-3alpha

To investigate the ability to eliminate CCR6-expressing cells, in vitro tests have been performed on the biotinylated MIP-3a coupled matrix. Blood was collected from blood donors and passed through the column device containing biotinylated MIP-3a coupled matrix. Blood samples were taken before and after column passage and analyzed by flow cytometry (FACS) for the depletion of CCR6-expressing cells.

Figure 6C:
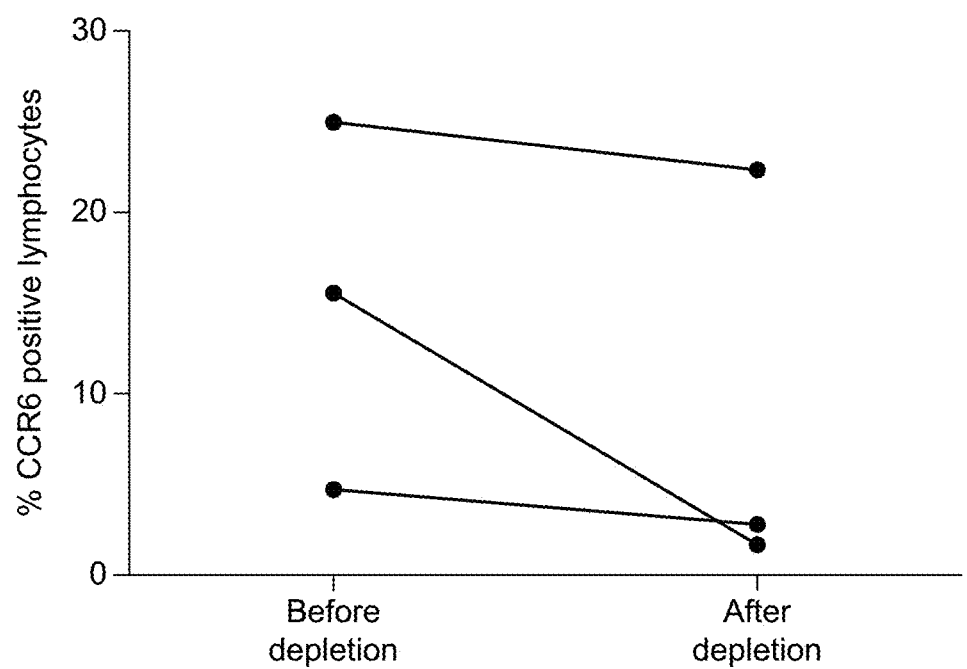
FIG. 6c—Results of in vitro depletion tests performed on the biotinylated MIP-3a coupled matrix showing ability to eliminate CCR6-expressing lymphocytes from blood from three healthy donors.

The results demonstrate significant depletion of the target population CCR6-expressing lymphocytes post matrix perfusion. Depletion tests were performed on blood from three healthy donors. The results are shown in FIG. 6c.

The in-vitro results demonstrate a specific reduction of up to around 15% of the CCR6-expressing cells by the column. Non-CCR6-expressing cells remained unaffected (data not shown).

The RANTES molecule was synthesized by Almac. The amino acid sequence of the biotinylated RANTES molecule is set forth as SEQ ID NO: 17:

```
H2N-
SPYSSDTTPCCFAYIARPLPRAHIKEYFYTSGKCSNPAVVFVTRKNRQVC
ANPEKKWVREYINSLEKS-CO2H
```

This molecule has the naturally occurring methionine at position 67 replaced with lysine to facilitate biotinylation at position 67.

Figure 12:
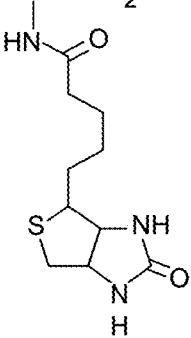
Figure 13:
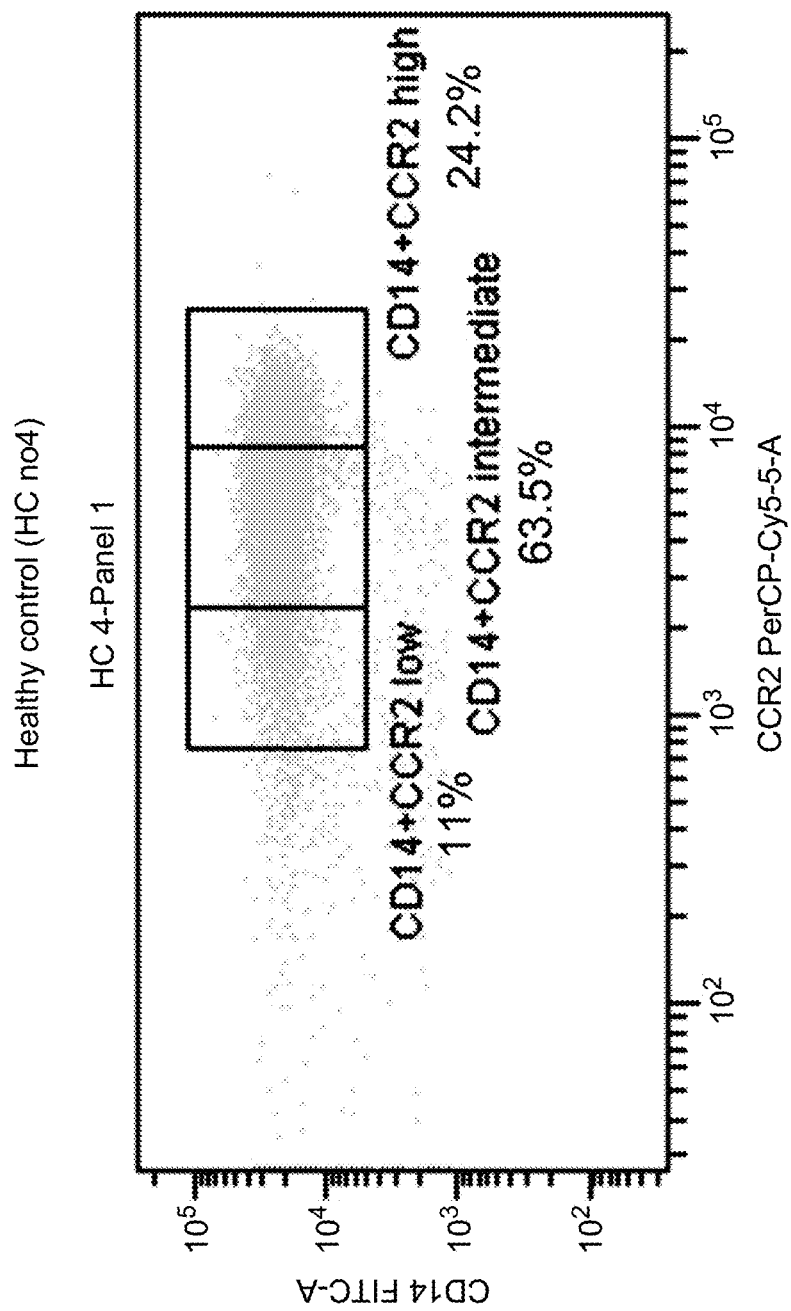

The side-chain of Lys 67 was directly biotinylated to given the protein primary structure shown in FIG. 12. The protein was folded and disulphide bonds formed between the first and third cysteine in the sequence and between the 2nd and 4th cysteines.

Example 4—MCP1 Derivatives

MCP-1 has been produced with residue 75 as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 1,

```
MKVSAALLCL LLIAATFIPQ GLAQPDAINA PVTCCYNFTN
RKISVQRLAS YRRITSSKCP KEAVIFKTIV AKEICADPKQ
KWVQDSMDHL DKQTQTPKT
```

The amino acid sequence of the mature protein is set forth as SEQ ID NO: 2,

```
QPDAINA PVTCCYNFTN RKISVQRLAS YRRITSSKCP
KEAVIFKTIV AKEICADPKQ KWVQDSXDHL DKQTQTPKT
```

X=Met or Nleu

The inventors have determined that chemokines may display improved binding properties where the chemokine is biotinylated via a spacer group. The spacer may prevent the biotin group from impacting on the binding affinity of the chemokine.

Figure 7:
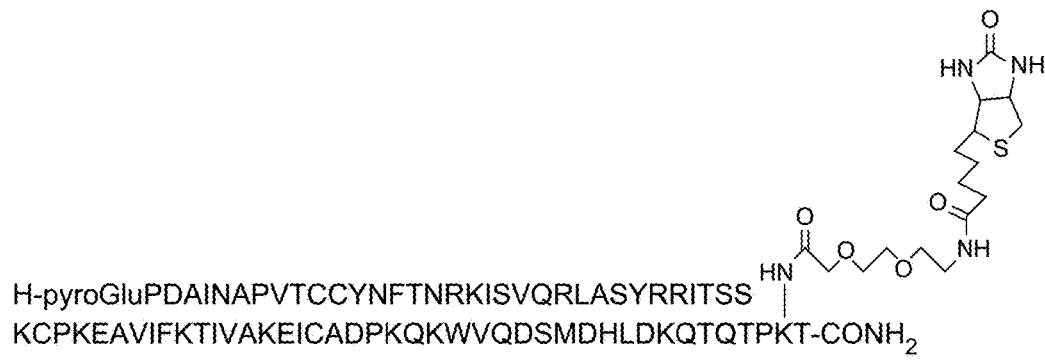
FIG. 7—Sequence and biotinylation, via a spacer group, of mature protein MCP-1 derivative containing Gln to pyroGlu modification FIG. 8—Sequence and biotinylation, via a spacer group, of mature protein MCP-1 derivative containing Gln to pyroGlu modification and Met to Norleu substitution FIG. 9—Sequence and biotinylation, via a spacer group, of truncated MCP-1 derivative containing Met to Norleu substitution FIG. 10—Alignment of MCP-1 and MCP-5 amino acid sequences FIG. 11—Sequence and biotinylation, via a spacer group, of (C-terminal) truncated MCP-5 derivative containing lie to Lys modification FIG. 12—Sequence and biotinylation, of RANTES derivative FIG. 13—example of gating criteria for CCR2 expressing monocytes FIG. 14a—Frequency of CCR2 positive T cells. Bars represent mean and SEM of T cells that express CCR2 in 2 patients and 20 healthy controls.

Thus, MCP-1 derivatised at the ε-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 7.

Figure 8:
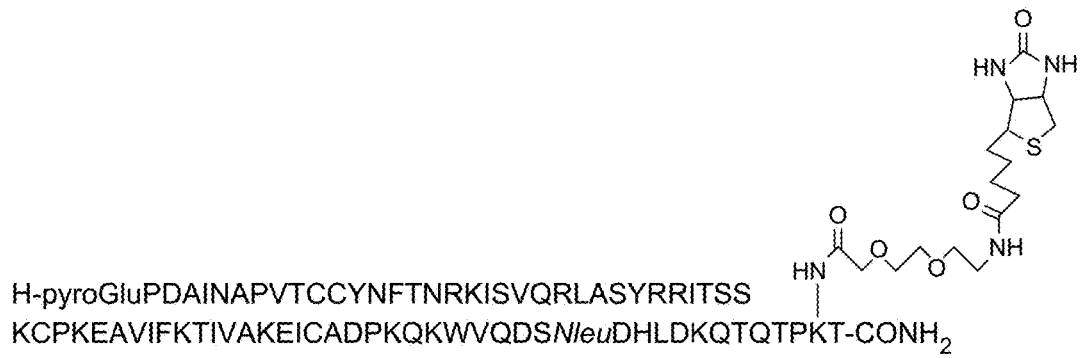

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 8 and in SEQ ID NO: 2.

Once synthesised, the activity of the various biotinMCP-1 derivatives will be determined in cell-based assays. In particular, agonist and antagonist properties will be determined in aequorin functional cell-based assay on human CCR2 receptor.

Example 5—Synthesis of a CCR2 Antagonist biotinMCP-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells (inhibition of chemotaxis IC50 20 nM)

The amino acid sequence of the truncated version is set forth as SED ID NO: 3:

```
VTCCYNFTN RKISVQRLAS YRRITSSKCP KEAVIFKTIV
AKEICADPKQ KWVQDSMDHL DKQTQTPKT
```

Figure 9:
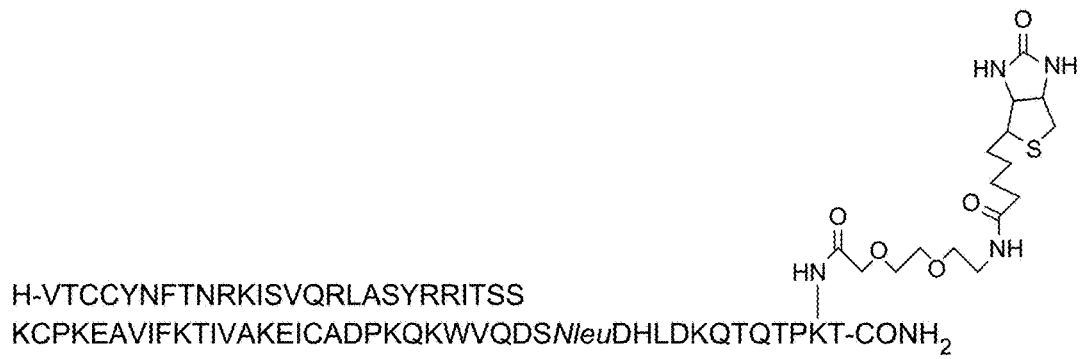

A derivative of this truncated version will be synthesised comprising residues 9 to 76 of the mature protein (MCP-1 9-76) with Met64 to Nleu substitution and derivatised at the ε-amino side chain functionality of Lys75 with PEG-Biotin (TFA salt). This molecule is shown schematically in FIG. 9. The PEG spacer will be 3,6,—dioxoaminooctanoic acid.

Once synthesised, the activity of the various biotinMCP-1 derivatives will be determined in cell-based assays. In particular, agonist and antagonist properties will be determined in aequorin functional cell-based assay on human CCR2 receptor.

Example 6—Demonstrate Removal of CCR2 Expressing Cells Using an Alternative Chemokine Ligand to MCP-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 4

```
MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG
```

The amino acid sequence of N-terminal processed MCP-5 chemokine is 82 amino acids long and is set forth as SEQ ID NO: 5

```
GPDAVSTP VTCCYNVVKQ KIHVRKLKSY RRITSSQCPR

EAVIFRTILD KEICADPKEK WVKNSINHLD KTSQTFILEP SCLG
```

An amino acid sequence alignment suggests that MCP-5 has a C-terminal extension when compared to the amino acid sequence of MCP-1. The results of this alignment are shown in FIG. 10. On this basis a C-terminal truncated version of MCP-5 will be synthesised. This truncated version will comprise MCP-5 residues 1-76, set forth as SEQ ID NO: 6:

```
GPDAVSTP VTCCYNVVKQ KIHVRKLKSY RRITSSQCPR

EAVIFRTILD KEICADPKEK WVKNSINHLD KTSQTFIL
```

In the truncated version, Ile75 to be substituted with Lys, set forth as SEQ ID NO: 7:

```
GPDAVSTP VTCCYNVVKQ KIHVRKLKSY RRITSSQCPR

EAVIFRTILD KEICADPKEK WVKNSINHLD KTSQTFKL
```

Figure 11:
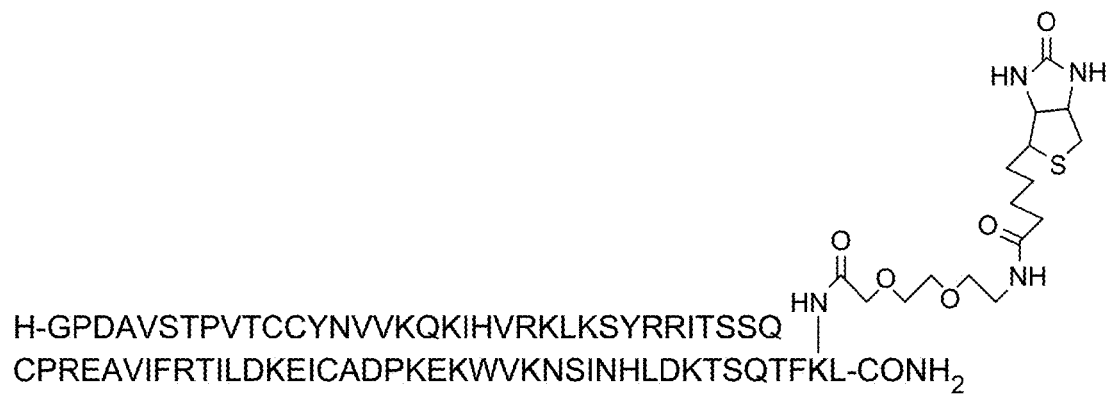

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 11.

Once synthesised, the activity of the various biotinMCP-5 derivatives will be determined in cell-based assays. In particular, agonist and antagonist properties will be determined in aequorin functional cell-based assay on human CCR2 receptor.

Examples 7 to 14

General Protocols for Chemokine Synthesis
Assembly:

Chemical synthesis of chemokines was performed using standard Fmoc solid phase peptides synthesis (SPPS) techniques on an ABI 433 peptide synthesiser. DIC (0.5M in DMF) and OxymaPure (0.5M in DMF) were used for activation, acetic anhydride (0.5M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:

1. Couple Fmoc-8-amino-3,6-dioctanoic acid (PEG)

Resin was swollen in DMF and then a solution of Fmoc-8-amino-3,6-dioctanoic acid (0.38 g, 1 mmol), DIC solution (2 ml, 0.5M in DMF) and OxymaPure solution (2 ml, 0.5M in DMF) was added. The mixture was sonicated for 3 hours and then washed with DMF.

2. Capping

The resin was capped with acetic anhydride solution (0.5M in DMF, 10 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (3481 µl) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 µl), thioanisole (500 µl), water (500 µl), DMS (500 µl), EDT (250 µl), NH$_4$I (500 µg) and phenol (500 µg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 7—biotinMCP-1 (CCL2)

Target Molecule: MCP-1 derivatised at the ε-amino side chain functionality of Lys(75) with PEG-Biotin (TFA salt)

Modifications: Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 8) is shown, prior to attachment of the PEG spacer and biotin molecules at amino acid 75 (K):

H-XPDAINAPVTCCYNFTNRKISVQRLASYRRITSSKCPKEAVIFKTIV
AKEICADPKQKWVQDSMDHLDKQTQTPKT-NH$_2$

X=pyroGlu

The engineered MCP-1 sequence was assembled on a solid support (Rink Amide resin), using Fmoc protocols for solid-phase peptide synthesis as described in the general protocols section:

H-XPDAINAPVTCCYNFTNRKISVQRLASYRRITSSKCPKEAVIFKTIV
AKEICADPKQKWVQDSMDHLDKQTQTPXT-RESIN

X1=pyroGlu
X75=K(ivDde)

FmocLys(ivDde)-OH was incorporated as residue 75 to facilitate site-specific labelling at this position of the protein (SEQ ID NO: 9). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 10):

H-XPDAINAPVTCCYNFTNRKISVQRLASYRRITSSKCPKEAVIFKTIV
AKEICADPKQKWVQDSMDHLDKQTQTPXT-NH$_2$

X1=pyroGlu
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-1: obtained=9032.8 Da; expected 9034.4 Da.
Functional Assay Data:
biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 8—biotinMCP-2 (CCL8)

Target Molecule: MCP-2 derivatised at the ε-amino side chain functionality of Lys(75) with PEG-Biotin (TFA salt)
Modifications: Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 11) is shown, prior to attachment of the PEG spacer and biotin molecules at amino acid 75 (K):

H-XPDSVSIPITCCFNVINRKIPIQRLESYTRITNIQCPKEAVIFKTKRG
KEVCADPKERWVRDSMKHLDQIFQNLKP-NH$_2$

X=pyroGlu

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG
KEVCADPKERWVRDSMKHLDQIFQNLXP-NH$_2$

X1=pyroGlu
X75=K(ivDde)

FmocLys(ivDde)-OH was incorporated as residue 75 to facilitate site-specific labelling at this position of the protein (SEQ ID NO: 12). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 13):

H-XPDSVSIPITCCFNVINRKIPIQRLESYTRITNIQCPKEAVIFKTKR
GKEVCADPKERWVRDSMKHLDQIFQNLXP-NH$_2$

X1=pyroGlu
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.
Functional Assay Data:
biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 9—biotinEotaxin (CCL11)

Target Molecule: Eotaxin derivatised at the ε-amino side chain functionality of Lys(73) with PEG-Biotin (TFA salt)
Modifications: Human eotaxin corresponding to residues 1-74, is initially expressed as 97 amino acids comprising the chemokine fold, and a 23 amino acid signal peptide which is cleaved off. The naturally occurring lysine at position 73 was modified through biotinylation on the resin. A PEG spacer was incorporated between the ε-amino functionality and the biotin.

The linear amino acid sequence (SEQ ID NO: 14) is shown, prior to attachment of the PEG spacer and biotin molecules at amino acid 73 (K):

H-GPASVPTTCCFNLANRKIPLQRLESYRRITSGKCPQKAVIFKTKL
AKDICADPKKKWVQDSMKYLDQKSPTPXP-NH$_2$

X is an amino acid residue that can be biotinylated, such as lysine, ornithine or diaminopropionic acid and optionally is biotinylated, optionally via a spacer molecule such as PEG, e.g. K(PEG-Biotin).

The engineered eotaxin sequence was assembled on a solid support (Rink Amide resin), using Fmoc protocols for solid-phase peptide synthesis as described in the general protocols section:

H-GPASVPTTCCFNLANRKIPLQRLESYRRITSGKCPQKAVIFKTKLA

KDICADPKKKWVQDSMKYLDQKSPTPXP-$NH_2$

X is K(ivDde)

FmocLys(ivDde)-OH was incorporated as residue 73 to facilitate site-specific labelling at this position of the protein (SEQ ID NO: 15). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 16):

H-GPASVPTTCCFNLANRKIPLQRLESYRRITSGKCPQKAVIFKTKLA

KDICADPKKKWVQDSMKYLDQKSPTPXP-$NH_2$

X is K(PEG-Biotin)

Electrospray ionisation with tandem mass spectrometry (ESi-TOF-MS) data of purified folded biotinEotaxin: obtained=8731.3 Da; expected 8731.3 Da.

Functional Assay Data:

biotinEotaxin was tested for activity in an Aequorin assay against hCCR3, (Euroscreen) and was shown to be an antagonist with an EC50 value of 211.8 nM. c.f. EC50 for recombinant native eotaxin is 10.7 nM (agonist).

Example 10—biotinRANTES (CCL5)

Target Molecule: RANTES derivatised at the ε-amino side chain functionality of Lys(67) with Biotin (TFA salt)

Modifications: Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 17) is shown, prior to attachment of the biotin molecule at amino acid 67 (K):

H-SPYSSDTTPCCFAYIARPLPRAHIKEYFYTSGKCSNPAVVFVTRKNR

QVCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)

FmocLys(ivDde)-OH was incorporated as residue 67 to facilitate site-specific labelling at this position of the protein (SEQ ID NO: 18). Subsequent removal of the ivDde protecting group, followed by coupling of the Biotin, was carried out as described in the general protocol section. Cleavage, purification and folding protocols were carried out as described to furnish the desired active chemokine (SEQ ID NO: 19).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 11—biotinMIP-3α (CCL20)

Target Molecule: MIP-3α derivatised at the ε-amino side chain functionality of Lys(68) with PEG-Biotin (TFA salt)

Modifications: Human MIP-3α corresponding to residues 1-70, is initially expressed as 96 amino acids comprising the chemokine fold, and a 26 amino acid signal peptide which is cleaved off. The naturally occurring lysine at position 68 was modified through biotinylation on the resin. A PEG spacer was incorporated between the ε-amino functionality and the biotin.

The linear amino acid sequence (SEQ ID NO: 20) is shown, prior to attachment of the PEG spacer and biotin molecules at amino acid 68 (K):

H-ASNFDCCLGYTDRILHPKFIVGFTRQLANEGCDINAIIFHTKKKLSVC

ANPKQTWVKYIVRLLSKKVKNM-OH

The engineered MIP-3α sequence was assembled on a solid support (Wang resin), using Fmoc protocols for solid-phase peptide synthesis as described in the general protocols section:

H-ASNFDCCLGYTDRILHPKFIVGFTRQLANEGCDINAIIFHTKKKLSVC

ANPKQTWVKYIVRLLSKKVXNM-RESIN

X=K(ivDde)

FmocLys(ivDde)-OH was incorporated as residue 68 to facilitate site-specific labelling at this position of the protein (SEQ ID NO: 21). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 22).

H-ASNFDCCLGYTDRILHPKFIVGFTRQLANEGCDINAIIFHTKKKLSVC

ANPKQTWVKYIVRLLSKKVXNM-OH

X is an amino acid residue that can be biotinylated, such as lysine, ornithine or diaminopropionic acid and optionally is biotinylated, optionally via a spacer molecule such as PEG, in particular K(PEG-Biotin)

Electrospray ionisation with tandem mass spectrometry (ESI-TOF-MS) data of purified folded biotinMip-3α: obtained=8396.4 Da; expected 8397.0 Da.

Functional Assay Data:

BiotinMIP-3α was tested for agonist activity in an Aequorin assay against hCCR6, (Euroscreen) and an EC50 value of 1.6 nM was reported. c.f. EC50 for recombinant native MIP-3α is 1.0 nM.

Example 12—biotinTECK (CCL25)

Target Molecule: TECK (Met to Nleu substitution) derivatised at the ε-amino side chain functionality of Lys72 with PEG-Biotin (TFA salt)

Modifications: Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 23) is shown, prior to attachment of the PEG spacer and biotin molecules at amino acid 72 (K):

H-XGVFEDCCLAYHYPIGWAVLRRAWTYRIQEVSGSCNLPAAIFYLPKRH

RKVCGNPKSREVQRAXKLLDARNKVF-OH

X1=pyroGlu or Gln
X64=Norleucine

The engineered TECK sequence was assembled on a solid support (Wang resin), using Fmoc protocols for solid-phase peptide synthesis as described in the general protocols section:

H-XGVFEDCCLAYHYPIGWAVLRRAWTYRIQEVSGSCNLPAAIFYLPKRH

RKVCGNPKSREVQRAXKLLDARNXVF-RESIN

X1=pyroGlu or Gln
X64=Norleucine
X72=K(Dde)

NPKSREVQRANIeKLLDARNK(ivDde)VF-RESIN

FmocLys(ivDde)-OH was incorporated as residue 72 to facilitate site-specific labelling at this position of the protein (SEQ ID NO: 24). Subsequent removal of the ivDde protecting group, followed by coupling of the PEG spacer and Biotin, was carried out as described in the general protocol section. Cleavage, purification and folding protocols were carried out as described to furnish the desired active chemokine.

The final active chemokine thus has the following sequence (SEQ ID NO: 25):

H-XGVFEDCCLAYHYPIGWAVLRRAWTYRIQEVSGSCNLPAAIFYLPKRH

RKVCGNPKSREVQRAXKLLDARNXVF-OH

X1=pyroGlu or Gln
X64=norleucine
X72=an amino acid residue that can be biotinylated, such as lysine, ornithine or diaminopropionic acid and optionally is biotinylated, optionally via a spacer molecule such as PEG, such as K(PEG-Biotin)

Electrospray ionisation with tandem mass spectrometry (ESI-TOF-MS) data of purified folded biotinTECK(Met to Nleu substitution): obtained=8958.5 Da; expected 8959.6 Da.

Functional Assay Data:

biotinTECK(Met to Nleu substitution) was tested for agonist activity in an Aequorin assay against hCCR9, (Euroscreen) and an EC50 value of 63.6 nM was reported. c.f. EC50 for recombinant native TECK is 67.9 nM.

Example 13—biotinITAC (CXCL11)

Target Molecule: ITAC derivatised with Biotin at the ε-amino side chain functionality of an additional Lysine inserted at the C-terminus after a PEG spacer (TFA salt)

Modifications: Human ITAC corresponding to residues 1-73, is initially expressed as 94 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 26) is shown, prior to attachment of the PEG spacer, additional lysine and biotin molecules:

H-FPMFKRGRCLCIGPGVKAVKVADIEKASIMYPSNNCDKIEVIITLKEN

KGQRCLNPKSKQARLIIKKVERKNF-OH

The engineered ITAC sequence was assembled on a solid support (Wang resin), using Fmoc protocols for solid-phase peptide synthesis as described in the general protocols section:

H-FPMFKRGRCLCIGPGVKAVKVADIEKASIMYPSNNCDKIEVIITLKEN

KGQRCLNPKSKQARLIIKKVERKNFX-RESIN

X is PEG-K(ivDde)

Fmoc-12-amino-4,7,10-trioxadodecanoic acid followed by FmocLys(ivDde)-OH were incorporated at the C-terminus to facilitate site-specific labelling with biotin at the ε-amino side chain functionality of the additional Lys (SEQ ID NO: 27). Subsequent removal of the ivDde protecting group, followed by coupling of the Biotin, was carried out as described in the general protocol section. Cleavage, purification and folding protocols were carried out as described to furnish the desired active chemokine (SEQ ID NO: 28).

H-FPMFKRGRCLCIGPGVKAVKVADIEKASIMYPSNNCDKIEVIITLKEN

KGQRCLNPKSKQARLIIKKVERKNFX-OH

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

Electrospray ionisation with tandem mass spectrometry (ESI-TOF-MS) data of purified folded biotinITAC: obtained=8866.5 Da; expected 8860.6 Da.

Functional Assay Data:

biotinITAC was tested for agonist activity in an Aequorin assay against hCXCR3, (Euroscreen) and an EC50 value of 15.7 nM was reported. c.f. EC50 for recombinant native ITAC is 0.7 nM.

Example 14—biotinIP-10 (CXCL10)

Target Molecule: IP-10 derivatised with Biotin at the ε-amino side chain functionality of an additional Lysine inserted at the C-terminus after a PEG spacer (TFA salt)

Modifications: Human IP-10 corresponding to residues 1-77, is initially expressed as 98 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 29) is shown, prior to attachment of the PEG spacer, additional lysine and biotin molecules:

H-VPLSRTVRCTCISISNQPVNPRSLEKLEIIPASQFCPRVEIIATMKKK

GEKRCLNPESKAIKNLLKAVSKERSKRSP-OH

The engineered IP-10 sequence was assembled on a solid support (Wang resin), using Fmoc protocols for solid-phase peptide synthesis as described in the general protocols section:

H-VPLSRTVRCTCISISNQPVNPRSLEKLEIIPASQFCPRVEIIATMKKK

GEKRCLNPESKAIKNLLKAVSKERSKRSPX-RESIN

X is K(ivDde), optionally attached via a spacer such as PEG, e.g. -PEG-K(ivDde)

Fmoc-8-amino-3,6-dioctanoic acid followed by FmocLys (ivDde)-OH were incorporated at the C-terminus to facilitate site-specific labelling with biotin at the ε-amino side chain functionality of the additional Lys (SEQ ID NO: 30). Subsequent removal of the ivDde protecting group, followed by coupling of the Biotin, was carried out as described in the general protocol section. Cleavage, purification and folding protocols were carried out as described to furnish the desired active chemokine. The final active chemokine thus has the following sequence (SEQ ID NO: 31):

H-VPLSRTVRCTCISISNQPVNPRSLEKLEIIPASQFCPRVEIIATMKKK

GEKRCLNPESKAIKNLLKAVSKERSKRSPX-OH

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

Electrospray ionisation with tandem mass spectrometry (ESI-TOF-MS) data of purified folded biotinIP-10: obtained=9141.0 Da; expected 9141.9 Da.

Functional Assay Data:

BiotinIP-10 was tested for agonist activity in an Aequorin assay against hCXCR3, (Euroscreen) and an EC50 value of 8.7 nM was reported. c.f. EC50 for recombinant native IP-10 is 4.4 nM.

Example 15—MS Diagnosis and Treatment Based Upon CCR2 and CCR6 Expressing T-Cells Materials and Methods 1. Flow Cytometric Analysis of Peripheral Blood Peripheral blood from patients with Multiple Sclerosis and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM $NH_4Cl$, pH 7.5) for 15 min at 37° C. The cells were washed in PBS with 2% Bovine Growth Serum, incubated with 10% human serum for 15 min at room temperature (RT) and stained with antibodies (Table 2) at 4° C. for 30 min. The cells were analysed with flow cytometry on a FACS Canto flow cytometer with the FACSDiva software (BD Biosciences).

TABLE 2

List of antibodies for flow cytometric analysis.

| Antibody | Fluorophore | Supplier |
| --- | --- | --- |
| CD3 | V450 | BD Biosciences |
| CCR6 | PE | BD Biosciences |
| Streptavidin | PE, APC | Biolegend |
| CCR2 | PerCP Cy5.5 | Biolegend |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 μM) or the corresponding chemokine receptor antibody at 4° C. for 30 min (Table 2). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 μM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 2), analysed with flow cytometry and compared with cells from peripheral blood that had not been incubated with the chemokine-matrix.

Results and Discussion

1. Flow Cytometric Analysis of Peripheral Blood

Figure 14A:
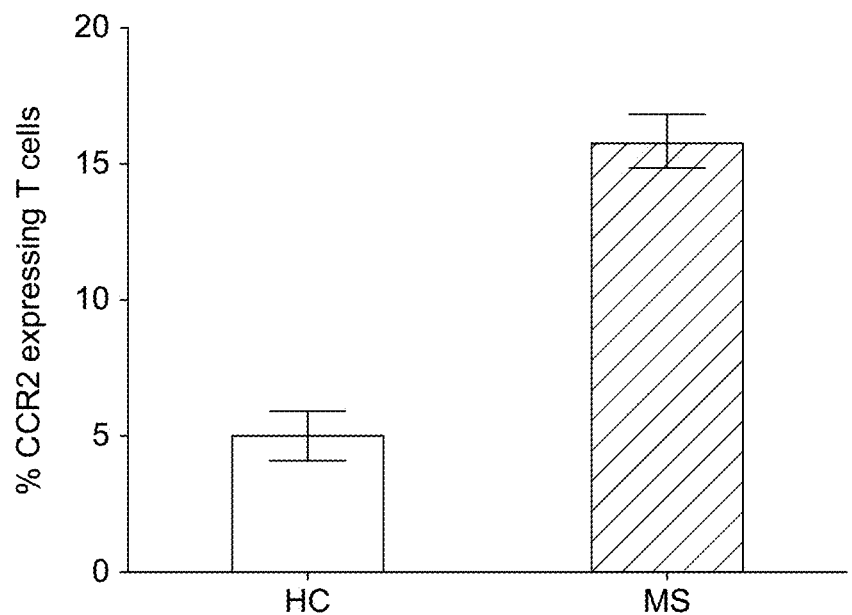
FIG. 14b—Frequency of CCR6 positive T cells. Bars represent mean and SEM of T cells that express CCR6 in 5 patients and 20 healthy controls. The expression of chemokine receptors and specific cell markers were analysed with flow cytometry. The T cells were characterized as CD3 positive.
Figure 14B:
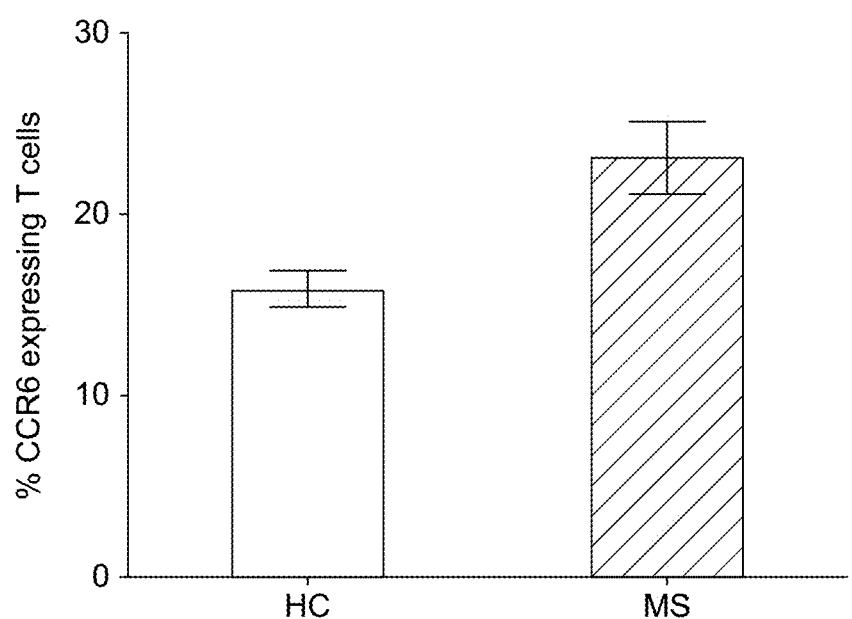

White blood cells from patients with Multiple Sclerosis (MS) were analysed for the expression of chemokine receptors with flow cytometry. The MS patients exhibited an increased frequency of circulating T cells that expressed the chemokine receptor CCR2, 15% compared to approximately 5% in healthy blood (FIG. 14a), based upon flow cytometry data and binding by an anti-CCR2 antibody. Furthermore, the patients had an increased frequency of T cells that expressed CCR6 (FIG. 14b).

2. Chemokine Binding Test

Figure 15A:
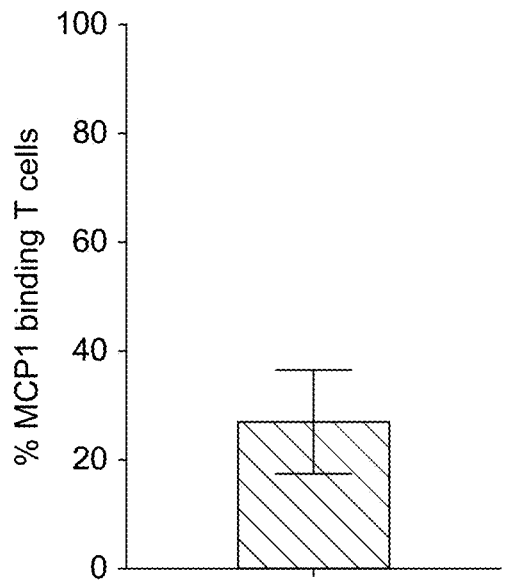
FIG. 15a—Binding of the chemokine bMCP-1 to T cells. Bar represents mean frequency and SEM of MCP-1 binding T cells in 5 patients with MS.
Figure 15B:
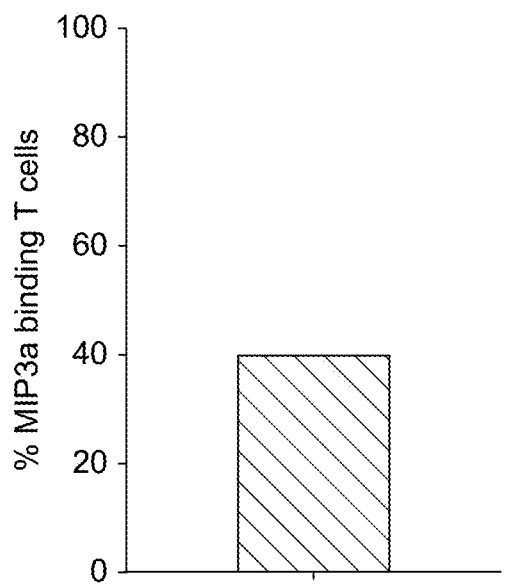
FIG. 15b—Binding of the chemokine bMIP3a to T cells. Bar represents frequency of MIP3a-binding T cells in 1 patient with MS. Blood was incubated with biotinylated chemokine and analysed with flow cytometry. The T cells were characterized as CD3 positive.

CCR2 binds to the chemokine MCP-1 that mediate migration and infiltration of inflammatory cells to various tissues. The ligand for CCR6 is MIP3a (CCL20) that can mediate migration of T cells into the CNS. Both these receptors are important in the inflammatory process. In accordance with the CCR2 and CCR6 expression, the T cells bound the biotinylated MCP-1 (bMCP-1) (FIG. 15a) and bMIP3a (FIG. 15b).

3. Cell Depletion by Matrix Conjugated with Biotinylated Chemokine

Figure 16A:
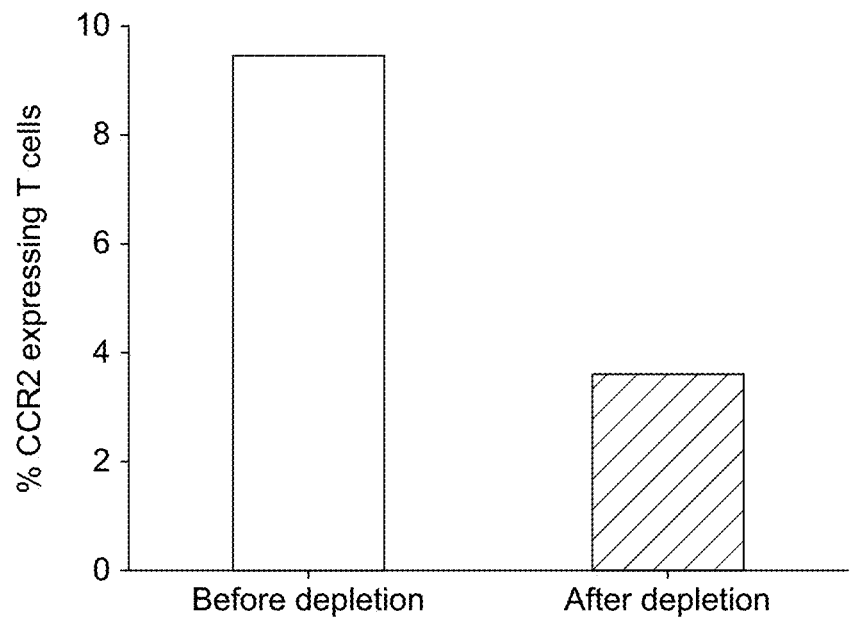
FIG. 16a—Depletion of CCR2 expressing T cells with Sepharose Streptavidin-matrix conjugated with bMCP-1.
Figure 16B:
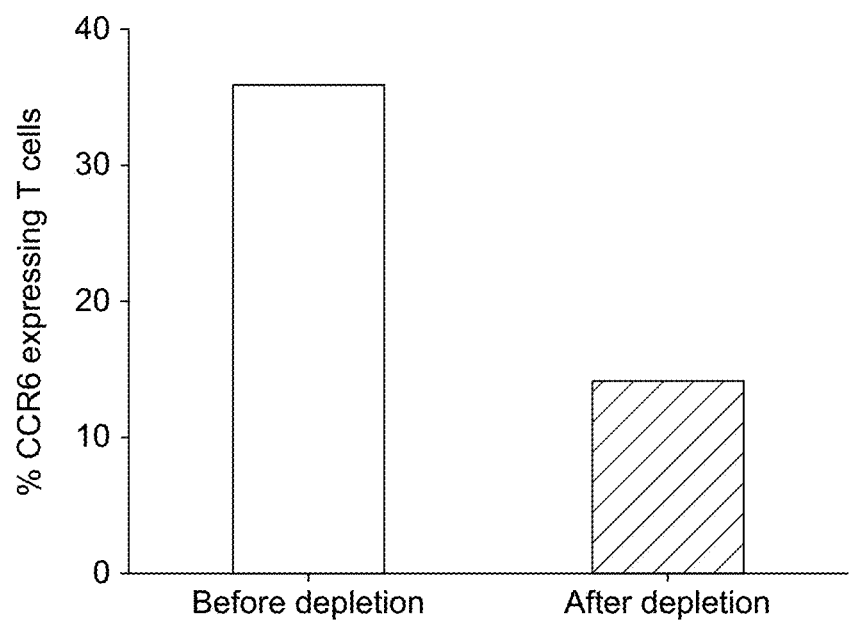
FIG. 16b—Depletion of CCR6 expressing T cells with Sepharose Streptavidin-matrix conjugated with bMIP3a. Blood cells from a patient with MS were incubated with biotinylated chemokine-Sepharose Streptavidin-matrix. Unbound cells were retrieved by washing the matrix. The cells (After Depletion) were then analysed with flow cytometry and compared with cells that had not been incubated with bchemokine-matrix (Before Depletion).

The CCR2 expressing T cells could be efficiently depleted with bMCP-1-conjugated Sepharose Streptavidin Matrix (FIG. 16a), and the CCR6 expressing T cells could be depleted with bMIP3a-conjugated Sepharose Streptavidin Matrix (FIG. 16b).

We conclude that the frequency of T cells that express CCR2 and CCR6 is enhanced in MS. These T cells can bind the ligands MCP-1 and MIP3a. Furthermore, the majority of the CCR2 and CCR6 expressing T cells can be removed with Sepharose Streptavidin matrix conjugated with the corresponding biotinylated chemokine.

The various embodiments of the present invention is not to be limited in scope by the specific embodiments described herein. Indeed, various modifications of the various embodiments of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

---

The invention claimed is:

1. A method for treating multiple sclerosis in a subject in need thereof comprising applying peripheral blood from the subject to an apheresis column loaded with a solid support comprising one or more binding reagents capable of specifically binding to a chemokine receptor CCR2 immobilized directly or indirectly on the support, whereby one or more cells expressing the chemokine receptor CCR2 are removed from the peripheral blood of the subject, wherein blood applied to the apheresis column is circulated back into the subject's systemic circulation, and whereby the multiple sclerosis is treated.

2. The method of claim 1, wherein the multiple sclerosis is selected from active and stable relapsing-remitting multiple sclerosis, primary progressive relapsing multiple sclerosis, secondary progressive relapsing multiple sclerosis, and progressive relapsing multiple sclerosis.

3. The method of claim 1, wherein the binding reagent is an agonist or an antagonist of CCR2.

4. The method of claim 1, wherein the binding reagent is an antibody or a chemokine.

5. The method of claim 4, wherein the chemokine is selected from MCP-1, MCP-2, MCP-3, MCP-4, and MCP-5.

6. The method of claim 5, wherein the chemokine is MCP-1 or MCP-5.

7. The method of claim 1, wherein the one or more cells are selected from monocytes, lymphocytes, neutrophils, macrophages, eosinophils, and basophils.

8. The method of claim 1, wherein the subject has increased levels of expression of CCR2 as compared to a subject that does not have multiple sclerosis.

9. The method of claim 1, wherein 20-50% of the subject's blood is applied to the column in a single treatment.

* * * * *